United States Patent [19]
Burns et al.

[11] Patent Number: 5,728,064
[45] Date of Patent: Mar. 17, 1998

[54] BALLOON CATHETER WITH IMPROVED PRESSURE SOURCE

[75] Inventors: Matthew M. Burns, Orono; Daniel M. Lafontaine, Plymouth, both of Minn.

[73] Assignee: SCIMED Life Systems, Inc., Maple Grove, Minn.

[21] Appl. No.: 619,375

[22] Filed: May 21, 1996

Related U.S. Application Data

[63] Continuation of Ser. No. 308,025, Sep. 16, 1994, Pat. No. 5,545,133.

[51] Int. Cl.$^6$ .................................................. A61M 29/00
[52] U.S. Cl. .............................. 604/96; 604/99; 606/192
[58] Field of Search .............................. 604/96, 97, 99, 604/100, 101, 186; 606/192–195

[56] References Cited

U.S. PATENT DOCUMENTS

| | | |
|---|---|---|
| 3,190,291 | 6/1965 | Foley . |
| 3,378,011 | 4/1968 | Vitello . |
| 3,379,197 | 4/1968 | Hayes . |
| 3,602,226 | 8/1971 | Ericson . |
| 3,675,658 | 7/1972 | Taylor . |
| 3,818,903 | 6/1974 | Bleecker . |
| 4,227,534 | 10/1980 | La Rosa . |
| 4,244,366 | 1/1981 | Raines . |
| 4,245,639 | 1/1981 | La Rosa . |

(List continued on next page.)

FOREIGN PATENT DOCUMENTS 2 209 121   5/1989   United Kingdom .

OTHER PUBLICATIONS

*Therapy and Prevention Congenital Heart Disease*, AHA Circulation brochure, "Angioplasty for coarctation of the aorta: long–term results", R. Cooper et al.; vol. 75, No. 3, pp. 600–604, Mar. 1987.

*European Heart Journal*, "Anterograde percutaneous transseptal valvuloplasty in a case of severe calcific aortic stenosis", vol. 8, pp. 190–193, Feb. 1987.

*Clinical Cardiology*, "Balloon Aortic Valvuloplasty in Children", vol. 13, pp. 458–466, Jul. 1990.

"Angiographic Patterns of Balloon Inflation During Percutaneous Transluminal Coronary Angioplasty: Role of Pressure–Diameter Curves in Studying Distensibility and Elasticity of the Stenotic Lesion and the Mechanism of Dilation," Hjemdahl–Monsen et al., *Journal of the American College of Cardiology*, vol. 16, No. 3, pp. 569–575, Sep. 1990.

"High Intensity Ultrasound Increases Distensibility of Calcific Atherosclerotic Arteries," Demer et al., *Journal of the American College of Cardiology*, vol. 18, No. 5, pp. 1259–1262, Nov. 1991.

"Balloon Catheters and Transluminal Dilatation: Technical Considerations," John Abele, *American Journal of Roentgenology*, vol. 135, pp. 901–906, Nov. 1980.

*Primary Examiner*—John D. Yasko
*Attorney, Agent, or Firm*—Robert E. Atkinson

[57] ABSTRACT

A balloon catheter having a long shaft with an inflatable balloon connected to its distal end with a pressure source connected to the shaft at an invivo point which operates to inflate and deflate the balloon. The balloon catheter may be a fixed-wire type, an over-the-wire type, or an single-operator-exchange type catheter. The pressure source may include a piston and a chamber with an actuation member attached to the piston. The actuation member may be a solid rod or a hollow robe. In the case where the actuation member is a hollow tube, the tube may be used to introduce inflation fluid into the pressure source and the inflation lumen. A receptacle such as a reel or tubular hoop may be used to contain the actuation member when pulled proximally. A pressure sensor/gauge and a balloon sizing scale may be incorporated into the catheter assembly to assist the treating physician in monitoring the procedure. A longitudinally oscillating drive, such as a solenoid, may be operatively connected to the pressure source.

33 Claims, 18 Drawing Sheets

U.S. PATENT DOCUMENTS

| | | |
|---|---|---|
| 4,332,254 | 6/1982 | Lundquist . |
| 4,370,982 | 2/1983 | Reilly . |
| 4,413,989 | 11/1983 | Schjeldahl et al. . |
| 4,429,724 | 2/1984 | Dorros et al. . |
| 4,439,185 | 3/1984 | Lundquist . |
| 4,446,867 | 5/1984 | Leveen et al. . |
| 4,476,866 | 10/1984 | Chin . |
| 4,535,757 | 8/1985 | Webster, Jr. . |
| 4,592,364 | 6/1986 | Pinto . |
| 4,651,738 | 3/1987 | Demer et al. . |
| 4,655,749 | 4/1987 | Fischione . |
| 4,723,938 | 2/1988 | Goodwin et al. ............ 604/99 |
| 4,740,203 | 4/1988 | Hoskins et al. . |
| 4,758,223 | 7/1988 | Rydell . |
| 4,781,192 | 11/1988 | Demer . |
| 4,838,864 | 6/1989 | Peterson . |
| 4,878,903 | 11/1989 | Mueller . |
| 4,919,121 | 4/1990 | Rydell et al. ............ 604/97 |
| 4,929,238 | 5/1990 | Baum . |
| 4,930,341 | 6/1990 | Euteneuer . |
| 4,944,726 | 7/1990 | Hilal et al. . |
| 4,954,239 | 9/1990 | Mueller . |
| 5,004,472 | 4/1991 | Wallace . |
| 5,009,662 | 4/1991 | Wallace et al. . |
| 5,019,041 | 5/1991 | Robinson et al. . |
| 5,021,046 | 6/1991 | Wallace . |
| 5,113,868 | 5/1992 | Wise et al. . |
| 5,152,776 | 10/1992 | Pinchuk . |
| 5,156,598 | 10/1992 | Skakoon et al. . |
| 5,171,299 | 12/1992 | Heitzmann et al. . |
| 5,196,017 | 3/1993 | Silva et al. . |
| 5,209,728 | 5/1993 | Kraus et al. . |
| 5,215,523 | 6/1993 | Williams et al. . |
| 5,265,593 | 11/1993 | Odland . |
| 5,273,537 | 12/1993 | Haskvitz et al. . |
| 5,275,169 | 1/1994 | Afromowitz et al. . |
| 5,284,480 | 2/1994 | Porter et al. ............ 604/97 |
| 5,338,301 | 8/1994 | Diaz . |
| 5,342,304 | 8/1994 | Tacklind et al. ............ 604/99 |

Prior Art

Present Invention

Prior Art

Present Invention

Prior Art

Present Invention

Present Invention

Present Invention

BALLOON CATHETER WITH IMPROVED PRESSURE SOURCE

This is a continuation application of prior application Ser. No. 08/308,025, filed on Sep. 16, 1994 now U.S. Pat. No. 5,545,133.

FIELD OF THE INVENTION

The present invention generally relates to balloon catheters. More specifically, the present invention relates to balloon dilation catheters used for the treatment of vascular disease. Those skilled in the art will recognize the benefits of applying the present invention to similar fields not discussed herein.

BACKGROUND OF THE INVENTION

A wide variety of therapeutic techniques have been developed to correct or inhibit vascular diseases. Coronary artery disease (CAD), for example, is an adverse condition of the heart in which the blood flow to the heart muscle is partially or totally restricted by occlusive material in the coronary arteries which narrows the blood flow lumen. The occlusive materials deprive portions of the heart muscle of essential oxygenated blood.

CAD may be treated by a surgical technique referred to as coronary artery bypass graft (CABG) surgery. This surgical procedure involves supplementing blood flow to the heart muscle by grafting a non-native conduit such as a saphenous vein graft (SVG) to the heart. A first end of the SVG is connected to the ascending aorta (proximal to the occlusive material) and the other end is connected to the artery distal of the occlusive material. Although this technique has been useful for treating CAD in native coronary arteries, it is not uncommon for occlusive material to form over time in the SVG thereby necessitating additional therapy.

Percutaneous translumenal coronary angioplasty (PTCA) has gained wide acceptance as an effective and less invasive alternative to CABG surgery in certain patient groups. The PTCA procedure involves the use of an angioplasty balloon catheter, several types of which are well known in the art. The balloon catheter is inserted into the body via the femoral artery and navigated to the coronary arteries assisted by a guide catheter and (usually) a guide wire. The balloon is positioned across the restriction in the artery and subsequently inflated. The inflated balloon widens the restriction and restores blood flow to portions of the heart muscle previously deprived of oxygenated blood.

A PTCA balloon catheter is typically about 140 to 150 cm long and has a manifold at its proximal end and a balloon at its distal end. The manifold facilitates connection to an inflation device which is used to inflate and deflate the balloon. A PTCA balloon catheter also includes an inflation lumen extending through its entire length to facilitate the delivery of inflation fluid to and from the balloon. Depending on the type of catheter used, an inflation lumen may be circular in cross section or it .may be annular in cross section. Some catheters have an inflation lumen which is circular at the proximal end of the shaft and annular at the distal end of the shaft. Since, PTCA catheters are relatively small in profile in order to facilitate navigation through the vascular system, the inflation lumen extending through the shaft is proportionately small. The long length of a typical inflation lumen in combination with its relatively small size create a significant resistance to the flow of inflation fluid. Consequently, the time required to inflate and deflate the balloon is proportionately long. Because flow rates are proportional to pressure, the drag on the inflation fluid is particularly noticeable during balloon deflation when the maximum possible pressure gradient is 14.7 psi. The deflation time is significant because an excessively long deflation time will compromise the treating physician's ability to relieve aschemia and/or reestablish blood flow across the occlusion being dilated. Furthermore, the compliance of the inflation fluid, the inflation device and the entire structure defining the fluid path add to the delay in deflation and inflation. The compliance of the fluid system reduces the immediate responsiveness of the balloon to actuation of the inflation device.

An inflation device is typically capable of inflating to pressures of about 300 psi, and is capable of drawing a near perfect vacuum (perfect vacuum=-14.7 psi). An inflation device is usually in the form of a modified 20 cc syringe and typically includes a threaded plunger with a handle and lock mechanism, and a pressure gauge. Due to its size and weight, a typical inflation device is extremely bulky as compared to a PTCA catheter.

Prior art balloon dilation catheters and inflation devices have certain disadvantages which are desirable to overcome. For example, it is desirable to reduce the inflation/deflation time of a balloon catheter and increase the immediate responsiveness of the balloon. This would allow for a more rapid balloon deflation and thus relieve aschemia and other adverse reactions to prolonged balloon inflation. Reducing inflation/deflation time would also allow for more effective use of the pulsating balloon technique. Eliminating a significant amount of the fluid system compliance would allow the treating physician to better "feel" the response of the vascular restriction to the inflation of the balloon. These desirable aspects would improve the treating physician's capabilities to treat CAD.

It is also desirable to eliminate the need to use a bulky inflation device. Eliminating the need for an inflation device would, for example, reduce the number accessory devices needed in a procedure, reduce the number prepping procedures required, reduce the necessary storage space, and reduce the amount of medical waste generated in a procedure. All of these benefits would ultimately save a significant amount of time and expense on behalf of the treating physician, the medical support staff, the hospital and the patient.

SUMMARY OF THE INVENTION

The present invention overcomes the disadvantages of the prior art in a novel and non-obvious manner. One embodiment of the present invention is a balloon catheter having a long shaft with an inflatable balloon connected to its distal end. A pressure source is connected to the shaft at an invivo point between the proximal end of the shaft and the distal end of the shaft and operates to inflate and deflate the balloon. The balloon catheter may be a fixed-wire type, an over-the-wire type, or an single-operator-exchange type catheter. The pressure source may include a piston and a chamber with an actuation member attached to the piston. The actuation member may be a solid rod or a hollow tube. In the case where the actuation member is a hollow tube, the tube may be used to introduce inflation fluid into the pressure source and the inflation lumen. A receptacle such as a reel or tubular hoop may be used to contain the actuation member when pulled proximally. A pressure sensor/gauge and a balloon sizing scale may be incorporated into the catheter assembly to assist the treating physician in monitoring the procedure. A longitudinally oscillating drive, such as a solenoid, may be operatively connected to the pressure source.

Another embodiment of the present invention is a balloon catheter having a proximal shaft section partially inserted into the body, and a distal shaft section which extends further inside the body. The distal shaft section defines an inflation lumen which has a proximal end terminating adjacent the proximal end of the distal shaft section. A balloon is connected to the distal end of the distal shaft section and is in fluid communication with the inflation lumen. The balloon catheter may also include a prepping lumen extending through the proximal shaft section to facilitate the introduction of inflation fluid into the inflation lumen. A pressure sensor/gauge and a balloon sizing scale may also be incorporated into the catheter to assist the treating physician in monitoring the procedure.

Yet another embodiment of the present invention is a balloon catheter having a long shaft with a lumen extending through the shaft. An inflatable balloon is connected to the distal end of the shaft. A plunger is disposed in the lumen of the shaft, and an actuation member is connected to the plunger.

In practice, a method of using a balloon catheter (wherein the catheter includes a long shaft with an inflatable balloon connected to its distal end and a pressure source connected to the shaft at a point between the proximal end of the shaft and the distal end of the shaft) includes the steps of: (1) inserting the balloon catheter into a vascular system of a patient, (2) positioning the balloon adjacent a treatment site inside the vascular system, (3) actuating the pressure source to effectively inflate the balloon, (4) actuating the pressure source to effectively deflate the balloon, and (5) withdrawing the balloon catheter from the vascular system. The steps of inflating the balloon and deflating the balloon may be repeated in rapid succession at frequencies substantially within the subsonic or sonic range.

The advantages of the present invention can be fully appreciated with a thorough review of the entire specification and drawings. Those skilled in the art will appreciate other advantages not fully described herein. Furthermore, while the disclosure focuses on balloon catheters, those skilled in the art will recognize that the invention may be incorporated into other devices and methods of use without departing from the spirit of the invention.

BRIEF DESCRIPTION OF THE DRAWINGS

FIGS. 2a and 2b show sectioned views of two single-operator-exchange (SOE) catheter embodiments. FIGS. 3 and 4 show, respectively, sectioned views of a fixed-wire (FW) catheter embodiment and an over-the-wire (OTW) catheter embodiment.

FIGS. 14 and 15 show the balloon response to a single inflation and deflation. FIGS. 16 and 17 show the balloon response to a cyclic inflation and deflation. FIGS. 18 an 19 show the response of a synthetic vascular lesion to balloon dilation. FIGS. 20 and 21 show the balloon response to a solenoid driven pressure source.

DETAILED DESCRIPTION OF THE INVENTION

The following detailed description should be read with reference to the drawings in which like elements in different figures are numbered identically. The drawings, which are not necessarily to scale, depict selected embodiments and are not intended to limit the scope of the invention.

Examples of constructions, materials, dimensions and manufacturing processes are provided for selected elements. All other elements employ that which is known to those skilled in the field of the invention. Those skilled in the art will recognize that many of the examples have suitable alternatives which may also be utilized.

Figure 1:
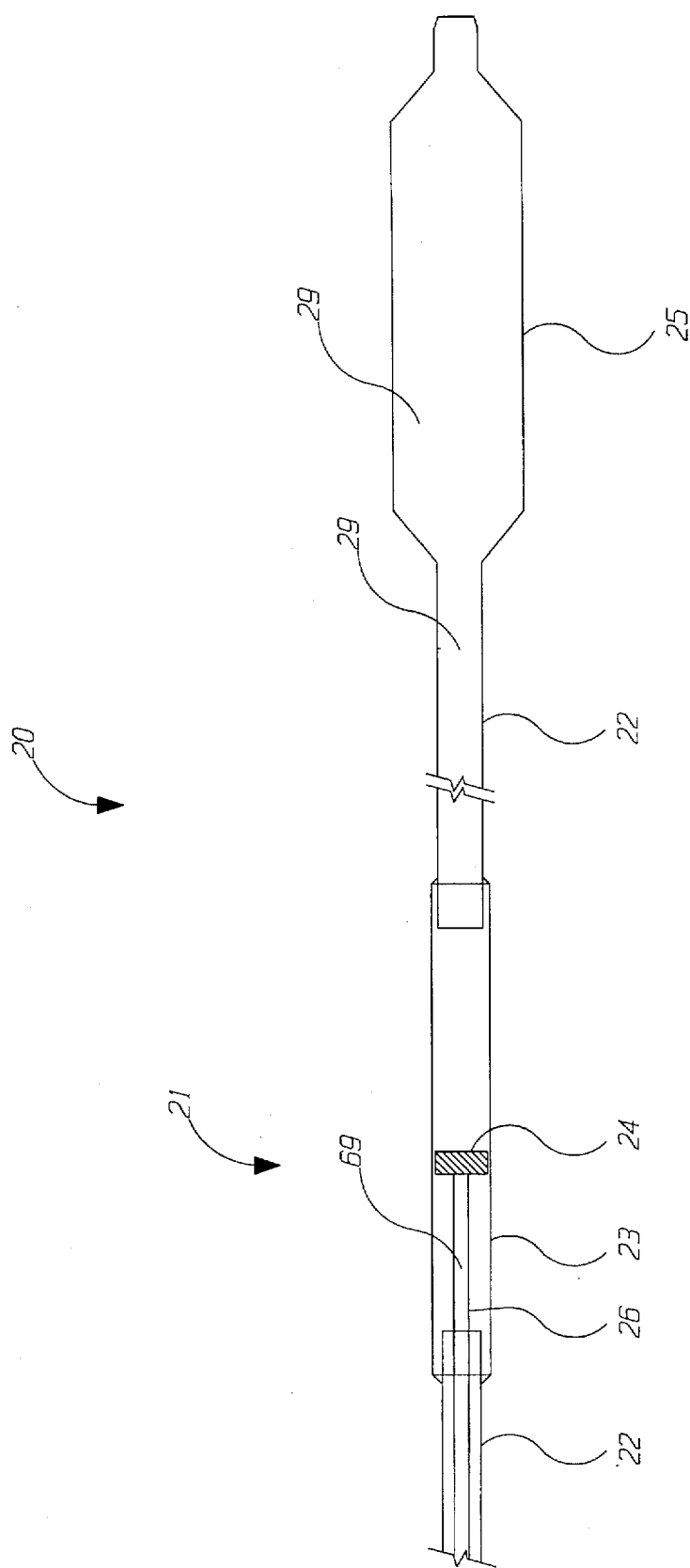
FIG. 1 is a schematic view of a generic embodiment of the present invention.

Referring to FIG. 1, a schematic view of an embodiment of the present invention is shown. Generic catheter 20 includes a shaft 22, a balloon 25 and a generic pressure source 21 connected to the shaft 22 at a location proximal of the balloon 25 and distal of the proximal end of the shaft 21. The pressure source may include a piston or plunger 24 disposed inside a chamber 23. An actuation member 26 may be connected to the piston 24 and extend proximally substantially parallel with the shaft 22.

The generic catheter 20 may take the form of any balloon catheter and used in a variety of medical procedures. For example, the generic catheter 20 may take the form of a SOE, FW or OTW type balloon catheter (FIGS. 2a and 2b, 3, 4 respectively) and may be used in coronary, peripheral, cerebral, and urethral applications. In addition, the catheter 20 may incorporate other clinically significant features such as perfusion or drug delivery capabilities. For the purpose of the following discussion, the exemplary embodiments are directed to a catheter system which is particularly suitable for PTCA procedures. However, with simple modifications in construction, the generic catheter 20 may be used for other medical applications not fully discussed herein.

The balloon 25 may also take on a variety of constructions. The material of the balloon 25 may be selected from polymers including, but not limited to, polyolefin copolymer, polyester, polyethylene teraphthalate, polyethylene, polyether-block-amide, polyamide, polyimide, nylon, latex and urethane. The balloon 25 may be made by blow molding a polymer extrusion into the desired shape. A number of ancillary processes may be used to affect the material properties of the balloon 25. For example, the polymer extrusion may be exposed to gamma radiation which alters the polymer infrastructure to provide uniform expansion during blow molding and additional burst strength when in use. In addition, the molded balloon 25 may be exposed to a low temperature plasma field which alters the surface properties of the balloon 25 to provide enhanced adhesion characteristics. Those skilled in the art will recognize that other materials and manufacturing processes may be used to provide a balloon 25 suitable for use with the present invention.

Similarly, the shaft 22 may be made of a several different constructions, materials and dimensions, depending on the performance characteristics desired. The shaft 22 may be made of, for example, an extruded polymer tube, a stainless steel hypotube, or a composite material such as stainless steel braid encased in polyimide. To impart different characteristics along the length of the catheter 20, the shaft 22 may incorporate changes in diameter or combine different constructions. For example, the shaft 22 may have a composite proximal section combined with a polymer distal section. Those skilled in the art will recognize that the shaft 22 can take on a wide variety of constructions not fully discussed herein but well known in the art.

Pressure source 21 is generic in form and may vary without departing from the scope of the invention. Specific embodiments of the pressure source 21 are discussed in more detail with reference to FIGS. 5 and 6. The generic pressure source 21 as shown in FIG. 1 is in fluid communication with the balloon 25 and when actuated, causes the balloon 25 to inflate or deflate. With the pressure source 21 located close to the balloon 25, the effective inflation lumen 29 is substantially shortened as compared to a conventional balloon catheter. The shortened inflation lumen reduces both the resistance to fluid flow and the compliance of the fluid path. Both these effects reduce the time required to inflate or deflate the balloon. The reduced deflation time allows the physician to more quickly relieve aschemia and other adverse reactions to prolonged balloon inflation. Eliminating a significant amount of the fluid system compliance allows the treating physician to better "feel" the response of the vascular restriction to the inflation of the baboon. In addition, pressure source 21 provides more immediate balloon response which is particularly effective for the pulsating balloon technique. The incorporation of the pressure source 21 also eliminates the need to use a bulky inflation device. Eliminating the need for an inflation device reduces the number accessory devices needed in a procedure, reduces the number prepping procedures required, reduces the necessary storage space, and reduces the amount of medical waste generated in a procedure, all of which would ultimately save a significant amount of time and expense.

The generic pressure source 21 includes a piston or plunger 24 disposed in a chamber 23. Pressure source 21 may operate much like a conventional syringe insofar as the general principles of fluid displacement and fluid pressure are concerned. The piston 24 may be virtually any given geometry sized to movably and sealingly fit into chamber 23 which is preferably incorporated into the shaft 22. The piston 24 may be displaced by several mechanisms including simple longitudinal actuation (e.g. a push member), rotational actuation (e.g. a threaded piston), or by magnetic actuation (e.g. a solenoid). As such, piston 24 may include an operably connected actuation member 26 which extends in a proximal direction from the piston 24 to a point where the treating physician has access to it and may actuate it to inflate or deflate the balloon 25. The actuation member 26 can function as a push member to longitudinally displace the piston 24 inside the chamber 23, the actuation member 26 can function as a rotating shaft to rotationally actuate a threaded piston (not shown), or the actuation member 26 can function as an electrical path to actuate a solenoid type piston (not shown). In addition, the actuation member 26 may be solid or tubular (shown) to provide a prep lumen 69 to carry inflation fluid to the pressure source 21, inflation lumen 29, and balloon 25 prior to use in-vivo. The inflation fluid may also be introduced by way of a syringe and needle insertable into the pressure source 21 or inflation lumen 29.

Figure 2A:
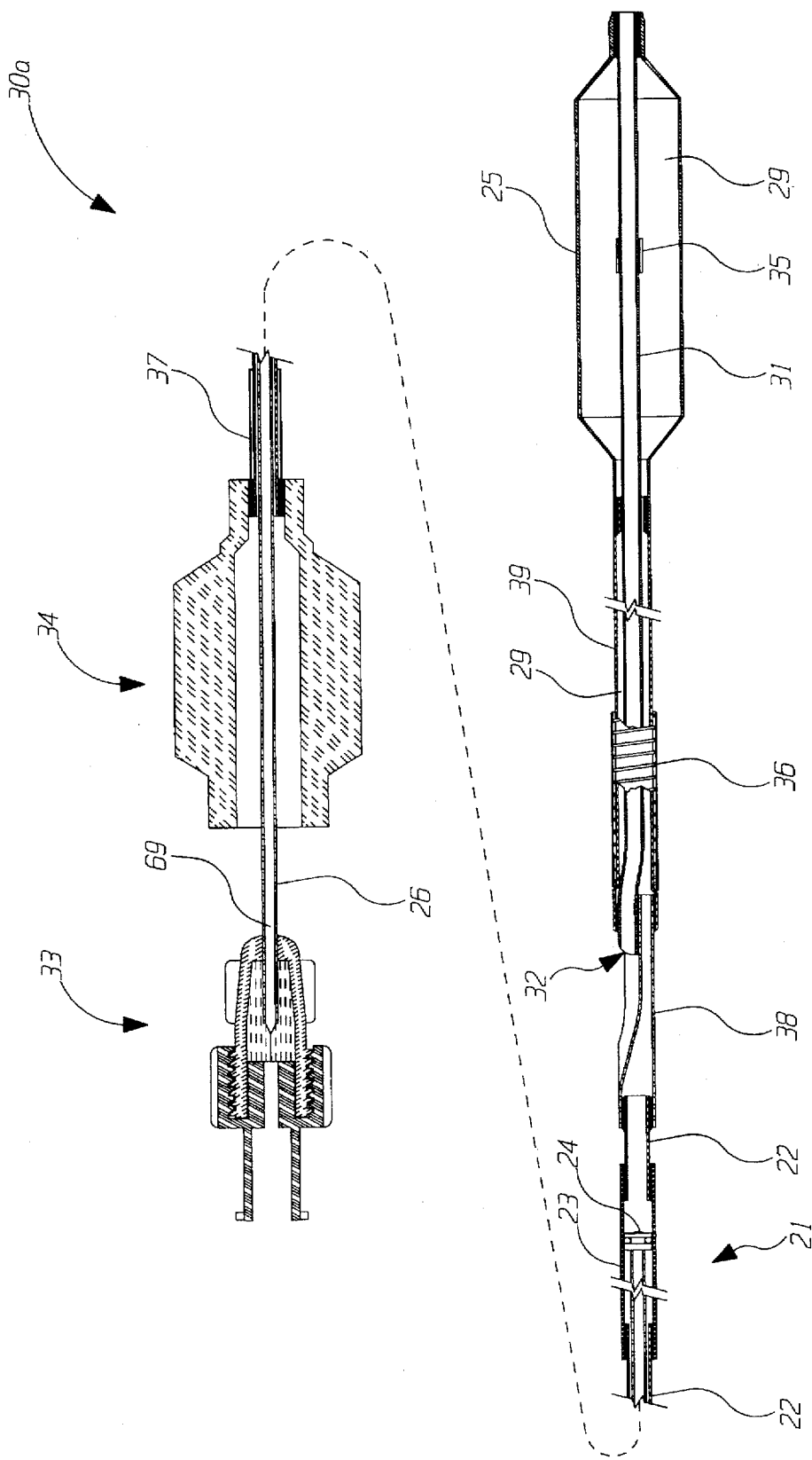
FIGS. 2a, 2b, 3, and 4 show specific examples of catheter embodiments utilizing some of the generic features shown in FIG. 1. In particular.

Referring now to FIG. 2a, a first SOE embodiment of the present invention is shown. A more detailed description of a known SOE catheter can be found in U.S. Pat. No. 5,156,594 to Keith et al. A difference between the Keith '594 and the SOE embodiments of the present invention is the use of the pressure source 21 with the associated components and necessary modifications. Another difference is the length of the guide wire lumen as compared to the length of the inflation lumen. In conventional SOE catheters, the length of the guide wire lumen is substantially shorter than the length of the inflation lumen. By contrast, the length of the inflation lumen in the present invention is essentially the same as the length of the guide wire lumen.

The SOE catheter 30a includes a guide wire tube 31 which extends from a point just distal of the balloon to a guide wire exit port 32 which is located proximal of the balloon 25 and near the location of the pressure source 21. Similarly, the inflation lumen 29 extends from a point adjacent the pressure source 21 to the interior of the balloon 25. Thus, as differentiated from conventional SOE catheters, the guide wire tube 31 is essentially the same length as the inflation lumen 29. The pressure source 21 and the guide wire exit port 32 are preferably positioned between 25 and 30 cm from the balloon 25.

SOE catheter 30a further includes shaft 22 which may be formed by conventional methods known to those skilled in the art. Since the primary function of the shaft 22 is to transmit longitudinal forces and not to carry inflation fluid, the shaft may have a non-integral structure. For example, it is contemplated that the shaft may be in the form of a plurality of braided wires, a hypotube with either longitudinal or helical slots, a loosely wound helical wire, or a closely wound wire coil. In the above examples, the shaft 22 may partially surround the actuation member 26. However, as discussed with reference to FIG. 2b, the shaft 22 may also extend along side the actuation member 26.

A manifold 34 and corresponding strain relief 37 are connected to the proximal end of the shaft 22 by conventional methods. Manifold 34 provides a means for the treating physician to more easily grip and manipulate the shaft 22. A crimp segment 38 is connected to the distal end of the shaft 22 by conventional methods and provides a transitional connection to the distal portion of the catheter including the guide wire tube 31 and the inflation tube 39. A coil strain relief 36 provides additional transitional support to reduce the potential for kinking the guide wire tube 31 and the outer tube 39. Balloon 25 is connected at its proximal end to the distal end of the outer tube 39 by conventional means. Similarly, the distal end of the balloon 25 is connected to the distal end of the guide wire tube 31. A radiopaque marker band 35 is secured to the guide wire tube 31 at a mid point inside the balloon 25. The radiopaque marker band 35 facilitates proper placement of the balloon 25 in-vivo.

Figure 5:
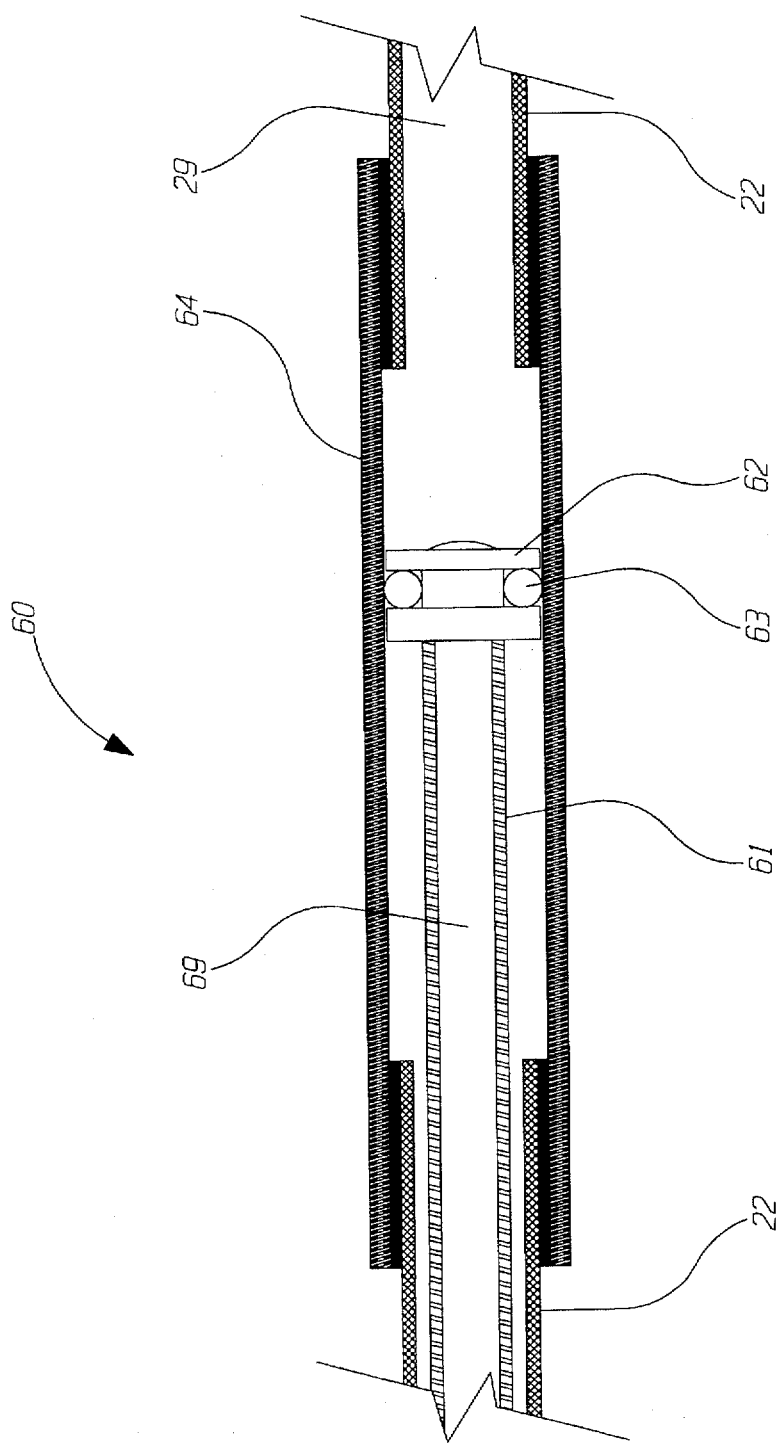
FIGS. 5 and 6 show specific examples of pressure sources which may, for example, be incorporated into the catheters described in FIGS. 2a–4.
Figure 6:
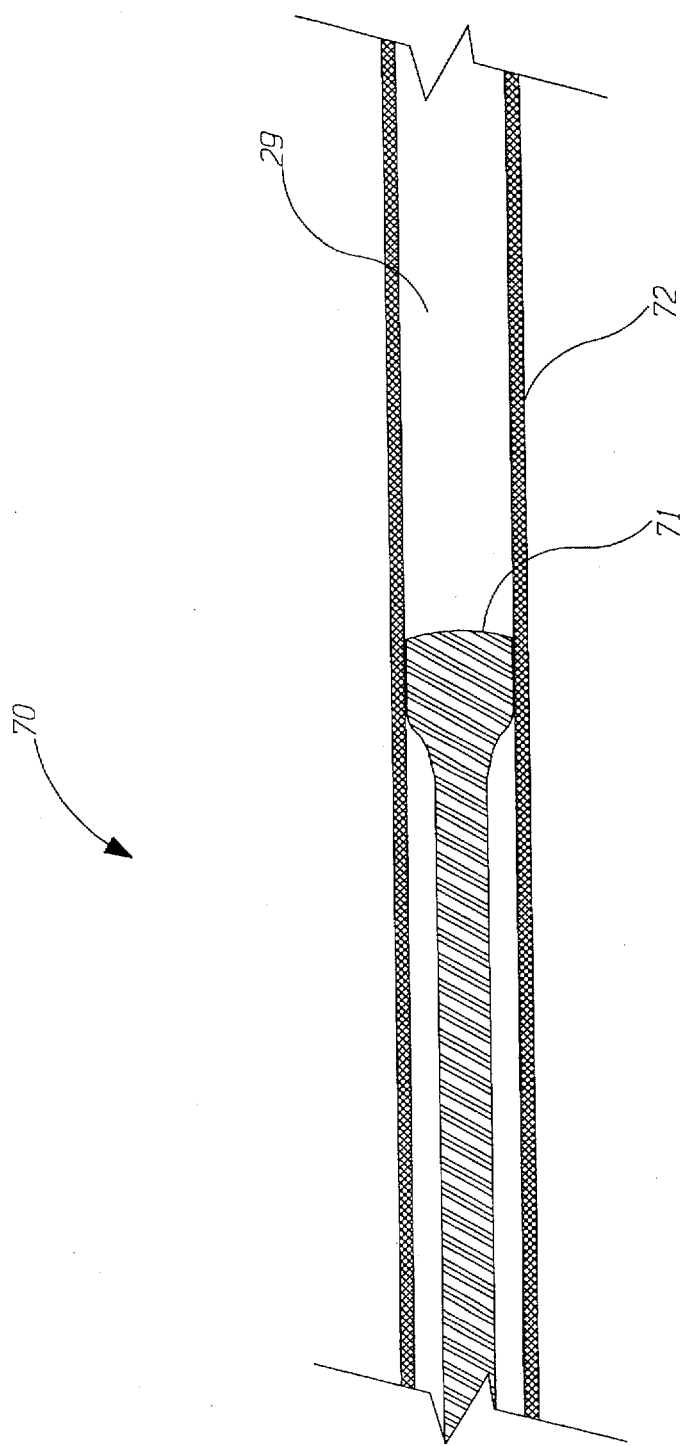

SOE catheter 30a utilizes pressure source 21 which includes piston 24, actuation member 26 and chamber 23 as discussed in detail with reference to FIG. 1. Pressure sources 60 and 70 as shown in FIGS. 5 and 6 respectively may be used in place of pressure source 21. Actuation member 26 may extend inside the shaft 22 (shown) or adjacent the shaft as mentioned above and discussed in detail with reference to FIG. 2b. A prep manifold 33 is connected to the proximal end of the actuation member 26 and is discussed in more detail with reference to FIG. 8. However, the proximal assembly as shown in FIG. 2a may take the form of any of the embodiments discussed with reference to FIGS. 7-13.

Figure 2B:
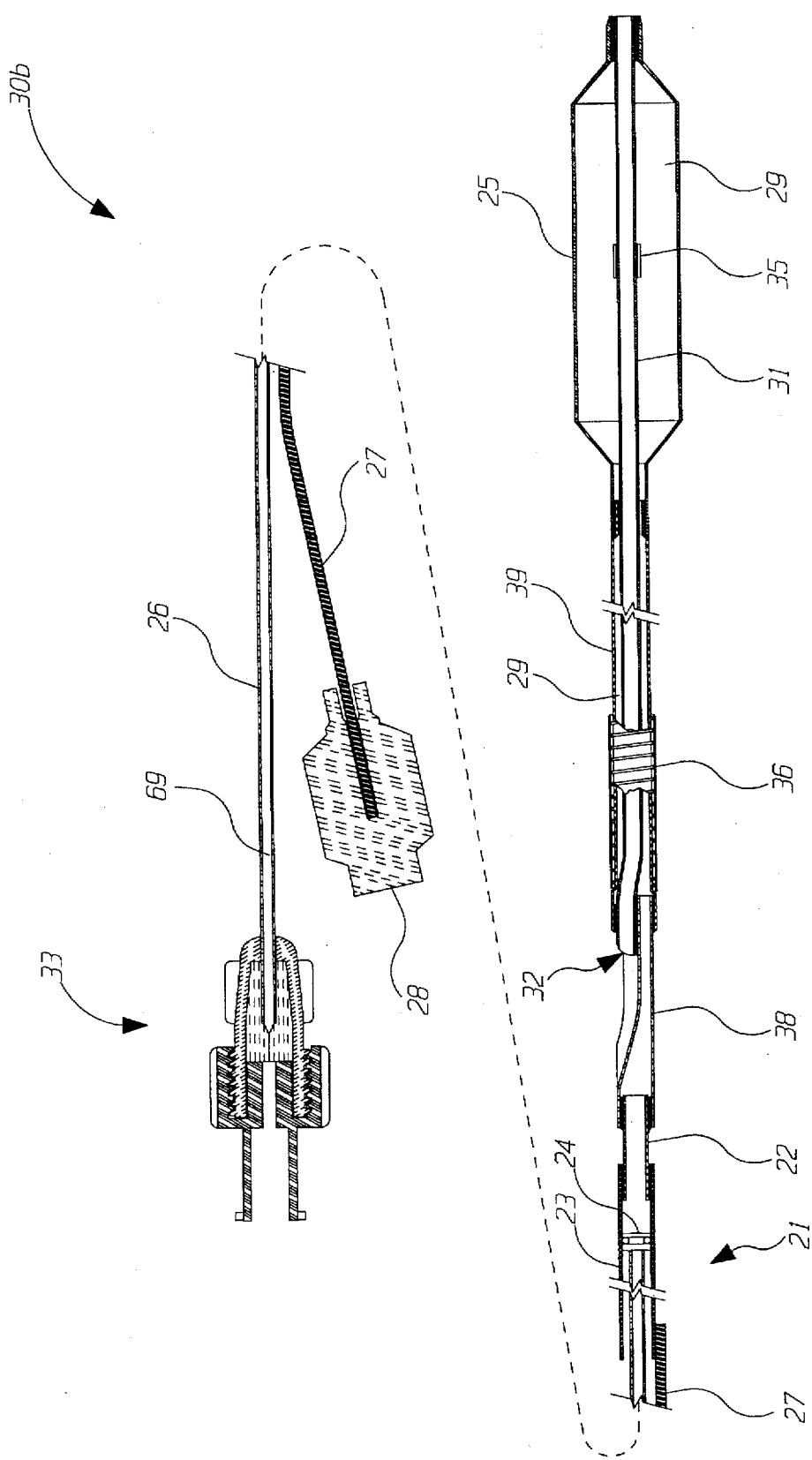

Now turning to FIG. 2b, a second SOE embodiment of the present invention is shown. The discussion with respect to SOE catheter 30a shown in FIG. 2a is equally applicable to SOE catheter 30b shown in FIG. 2b with the following exceptions. As stated previously, the primary function of the shaft 22 in FIG. 2a is to transmit longitudinal forces and not to carry inflation fluid. Thus, the shaft 22 may be replaced with shaft extension 27 which extends along side the actuation member 26. The shaft extension 27 provides a means to transmits longitudinal forces which facilitates manipulation of the catheter 30b and stabilization of the chamber 23 relative to the actuation member 26 and piston 24. The shaft extension 27 may be formed of 304v SST and may have a diameter of about 0.020 to 0.040 inches. An extension handle 28 is rigidly connected to the proximal end of the shaft extension 27 and provides a means for the treating physician to more easily grip and manipulate the shaft extension 27.

Figure 3:
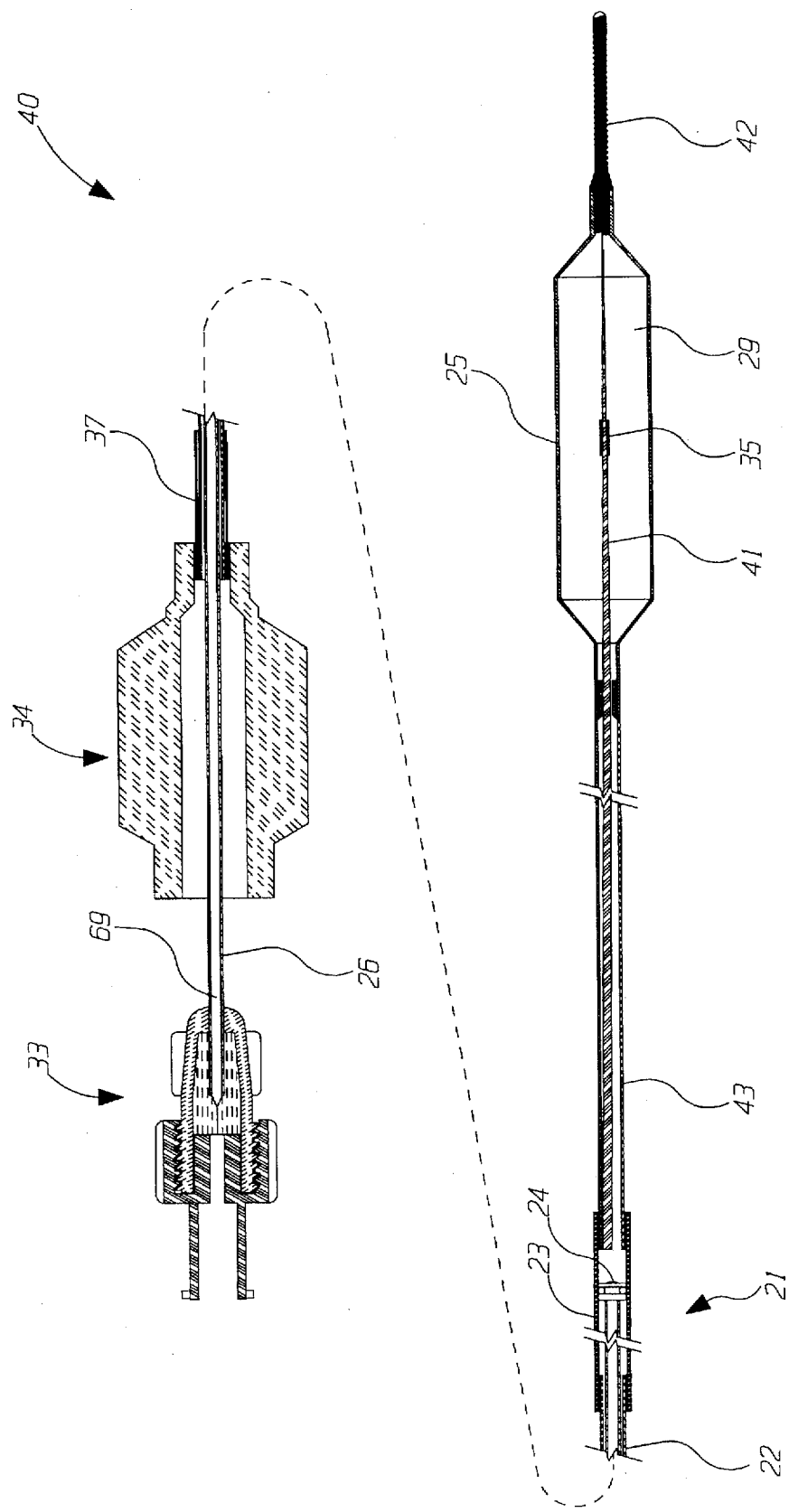

Referring now to FIG. 3, a FW embodiment of the present invention is shown. A more detailed description of a known FW catheter can be found in U.S. Pat. No. 4,943,278 to Euteneuer et al. A difference between Euteneuer '278 and the embodiment shown in FIG. 3 is the use of the pressure source 21 with the associated components and necessary modifications. FW catheter 40 utilizes pressure source 21 which includes piston 24, actuation member 26 and chamber 23 as discussed in detail with reference to FIG. 1. Pressure sources 60 and 70 as shown in FIGS. 5 and 6 respectively may be used in place of pressure source 21. Actuation member 26 may extend inside the shaft 22 (shown) or adjacent the shaft as discussed with reference to FIG. 2b. A prep manifold 33 is connected to the proximal end of the actuation member 26 and is discussed in more detail with reference to FIG. 8. However, the proximal assembly shown in FIG. 3 may take the form of any of the embodiments discussed with reference to FIGS. 7–13.

FW catheter 40 includes a core wire 41 which includes a spring tip 42 connected at its distal end. The proximal end of the core wire 41 may be connected to the distal end of the chamber 23 by a conventional means. An inflation tube 43 is connected at its proximal end to the distal end of the chamber and connected at its distal end to balloon 25. A radiopaque marker band 35 is secured to the core wire 41 at a mid point inside the balloon 25. The radiopaque marker band 35 facilitates proper placement of the balloon 25 in-vivo. A manifold 34 and corresponding strain relief 37 are connected at the proximal end of the shaft 22 by conventional methods. Manifold 34 allows the treating physician to more easily grip and manipulate the shaft 22.

Figure 4:
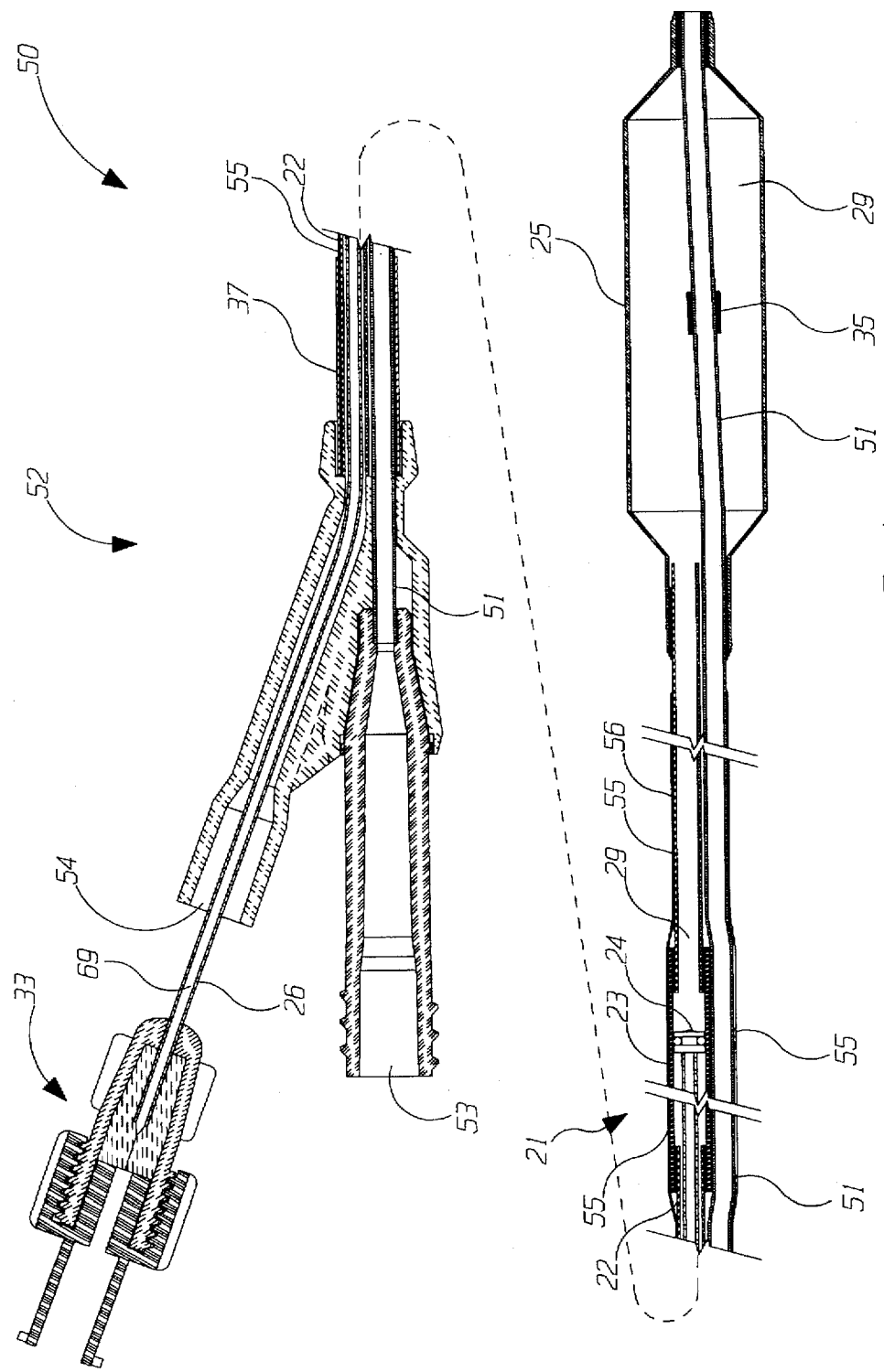

Referring now to FIG. 4, an OTW embodiment of the present invention is shown. A more detailed description of a known OTW catheter can be found in U.S. Pat. No. 5,100,381 to Burns. One significant difference between the device disclosed in Burns '381 and the OTW catheter 50 shown in FIG. 4 is the use of the pressure source 21 with the associated components and necessary modifications. As with SOE catheter 30a and FW catheter 40, OTW catheter 50 utilizes pressure source 21 which includes piston 24, actuation member 26 and chamber 23 as discussed in detail with reference to FIG. 1. Pressure sources 60 and 70 as shown in FIGS. 5 and 6 respectively may be used in place of pressure source 21. Actuation member 26 may extend inside the shaft 22 (shown) or adjacent the shaft as discussed with reference to FIG. 2b. A prep manifold 33 is connected to the proximal end of the actuation member 26 and is discussed in more detail with reference to FIG. 8. Note, however, that the proximal assembly shown in FIG. 4 may take the form of any of the embodiments discussed with reference to FIGS. 7–13.

OTW catheter 50 includes a guide wire tube 51 which extends the full length of the catheter 50. The distal end of the guide wire tube 51 is secured to the distal end of the balloon 25 by a conventional means. The proximal end of the balloon 25 is connected to a distal portion of the guide wire tube 51 and to the distal end of inflation tube 56. The proximal end of the inflation tube 56 is connected to the chamber 23 to provide a fluid path from the pressure source 21 to the balloon 25. The proximal end of the guide wire tube 51 is connected to a fairly conventional OTW manifold 52. Guide wire tube 51 is sized to slidably receive a guide wire by way of guide wire port 53 on manifold 52. The manifold 52 includes an actuation member port 54 which guides the actuation member 26 into the interior of the shaft 22. The manifold 52 may be connected to the shaft 22 and the guide wire tube 51 which allows fie treating physician to more easily grip and manipulate the catheter 50. The manifold 52 may also incorporate a strain relief 37 to reduce the potential for kinking the shaft 22 and the guide wire tube 51 adjacent the manifold 52. The shaft 22, the guide wire tube 51 and the inflation tube 56 may be connected along their length by several methods such as adhesive and/or an outer sheath 55. Alternatively, the entire shaft assembly could be made of a dual lumen extrusion with one lumen for a guide wire and the other lumen for the actuation member 26, the chamber 23 and the inflation lumen 29.

While the above description contemplates a construction wherein the guide wire tube 51 is adjacent (i.e. not coaxial) to the shaft 22 and the inflation lumen 56, it is also contemplated that a coaxial OTW catheter (not shown) may be made to incorporate a pressure source 21. In the coaxial construction, the guide wire tube would extend inside the actuation member, and the actuation member would in turn extend inside the shaft. The actuation member and the shaft would have a larger relative diameter than discussed in the non-coaxial embodiment in order to accommodate the guide wire tube. The chamber of the coaxial pressure source would be annular in cross section as defined by the outside surface of the guide wire tube and the inside surface of the shaft. The piston would be ring-shaped and sealingly slide around the guide wire tube and inside the shaft. The distal end of the guide wire tube would be connected to the distal end of the balloon and the shaft distal of the chamber would be connected to the proximal end of the balloon. A support connection may be desired between the guide wire tube and the shaft which would prevent relative longitudinal movement therebetween while allowing inflation fluid to pass through.

Now referring to FIG. 5, a preferred embodiment of a pressure source is shown. The generic pressure source 21 as seen in FIG. 1 may take the form of pressure source 60 shown in FIG. 5. Pressure source 60 provides all the advantages discussed with reference to generic pressure source 21. Pressure source 60 includes a piston head 62 disposed in a chamber 64 and connected to an actuation member 61. The piston head 62 includes an o-ring 63 to fluidly seal the piston inside the chamber 64 while permitting relatively free longitudinal movement. It is contemplated that more than one o-ring 63 may be desirable to provide a more effective fluid seal. The actuation member 61 may either be a solid rod or a hollow tube (shown) to facilitate the introduction of inflation fluid into the inflation lumen 29 and to facilitate pressure monitoring by a fluidic pressure gauge as discussed with reference to FIG. 9. Assuming inflation fluid is already disposed inside the pressure source 60 and the entire inflation lumen 29, longitudinal displacement d actuating member 61 by the treating physician causes corresponding longitudinal displacement of piston head 62. The displacement of piston head 62 and the sealing action of the o-ring 63 in turn causes fluid to be displaced into or out of the balloon, depending on the direction of the displacement. It is preferred that the piston head 62 be located at a position allowing for slight proximal displacement (creating a vacuum in the balloon) and substantial distal displacement (creating high positive pressures in the balloon).

The piston head 62, o-ring 63, and actuation member 61 may be manufactured as follows. Note that the dimensions and materials may be altered to achieve the desired performance characteristics. The actuation member 61 may be made of 304v stainless steel (SST) with an outer diameter of about 0.023 inches which is small enough to fit inside the shaft 22 but large enough to provide sufficient column strength to actuate the piston to high pressures. The inside diameter may be about 0.017 inches which is large enough to provide an adequate path for the introduction of inflation fluid into the inflation lumen 29 and the interior of the balloon. The inside diameter also affects the column strength of the actuation member 61 and should be sufficiently small relative to the outside diameter to reduce the potential for buckling. The length of the actuation member 61 should be sufficient to extend from a point outside the body to the pressure source 60 which is preferably located near the balloon to minimize the inflation fluid path. It is contemplated that the position of the pressure source be approximately 25-30 cm from the balloon for PTCA applications such that the pressure source remains substantially inside the guide catheter. As such, the length of the actuation member for PTCA applications is preferably about 115 cm.

The piston head 62 and the o-ring 63 may be mounted on the actuation member 61 by sequentially sliding parts onto the actuation member 61 and securing the parts at opposite ends. For example, the proximal end of the parts may be secured by soldering a short hypotube collar to the actuation member 61. A proximal polymer (e.g. polycarbonate) ring is slid on, followed by the o-ring 63, which is followed by a distal polymer ring. As mentioned previously, it may be desirable to utilize more than one o-ring to provide a more effective high pressure seal. The distal polymer ring may be secured with a suitable adhesive. The polymer rings are sized to provide a close fit in the chamber 64. The o-ring is sized to provide an interference fit in the chamber and thus provide a fluid seal, while permitting relatively free longitudinal displacement. The ends of the parts may be secured by other means, provided the proximal end is secured to withstand the high forces associated with distal actuation (inflating the balloon) and the distal end is secured to withstand relatively low forces associated with proximal actuation (deflating the balloon).

The chamber 64 may be formed of 304v SST, a high strength polymer such as polyimide, or a composite structure such as SST braid encased in polyimide. The chamber 64 may be a separate element (shown) secured at its ends to the shaft 22 by a suitable adhesive or it may be formed integrally with the shaft 22. The length and inside diameter of the chamber 64 must be sufficient to allow for both proximal actuation to generate a vacuum in the balloon (i.e. deflate the balloon) and distal actuation to inflate the balloon to high pressures (e.g. 300 psi.). For example, if a conventional PTCA balloon (20 mm length) is used, the resulting dimensions would be as shown in Table 1.

TABLE 1

| Balloon Diameter (mm) | Distal Stroke (inches) | Proximal Stroke (inches) | Chamber Length (inches) | Chamber Diameter (inches) |
|---|---|---|---|---|
| 1.5 | 2.75 | 1.0 | 3.75 | 0.030 |
| 2.0 | 3.75 | 1.0 | 4.75 | 0.035 |
| 2.5 | 5.0 | 1.0 | 6.0 | 0.040 |
| 3.0 | 5.75 | 1.0 | 6.75 | 0.045 |
| 3.5 | 6.5 | 1.0 | 7.5 | 0.050 |
| 4.0 | 7.25 | 1.0 | 8.25 | 0.055 |

With reference now to FIG. 6, another embodiment of a pressure source is shown. The pressure source 70 shown in FIG. 6 enjoys the same advantages discussed with reference to pressure source 21 as shown in FIG. 1 and is similar to pressure source 60 shown in FIG. 5 except for the following differences. Essentially, the pressure source 70 combines the plurality of parts of pressure source 60 into a single plunger 71. The shaft in turn functions as a chamber 72. The plunger 71 may be made of solid 304v SST and is preferably sized to provide a close fit inside the chamber 72 which thus provides an essentially fluid tight seal. The plunger 71 may continue proximally to a point outside the body to function as an actuation member. To reduce friction, it is contemplated that only the distal portion of the plunger 71 have a close fit with the inside of the chamber 72. Alternatively, to provide additional column strength, the diameter of the plunger may remain substantially constant along its entire length.

An alternative embodiment is contemplated in which a proximal seal is used to seal about the plunger 71 such that when the plunger 71 is inserted into the shaft 22, it displaces a volume of fluid into the balloon. This embodiment would not require a fluid tight fit between the distal end of the plunger 71 and the chamber 72. A seal located at the proximal end of the catheter would allow the plunger to be moved longitudinally while preventing fluid from escaping the system. The balloon would be inflated with a volume of fluid that is equal to the volume of the plunger 71 inserted into the shaft 22.

It is also contemplated that a magnetic solenoid (not shown) can be used to drive a pressure source similar to pressure source 60 or pressure source 70. The solenoid may either be located at the proximal end of the catheter assembly, incorporated into the catheter shaft 22, or incorporated into the pressure source. If the solenoid were incorporated into the pressure source, for example, the piston could be made of a magnetically responsive material and the chamber could incorporate a wire coil electrically connected to a control system and a power source. The power source and associated control system are substantially known in the art and may be modified to suit this particular application. By supplying the coils with an appropriate electrical signal, the coils would generate a magnetic field to longitudinally displace the piston in the desired direction. The longitudinal displacement would in turn cause the balloon to either inflate or deflate depending on the signal and the coil wind direction. It is also contemplated that a spring may be incorporated into the chamber to provide a force causing the magnetically actuated piston to return to its original position, such as a position generating a vacuum in the inflation lumen and balloon. Alternatively, a secondary coil (wound in the opposite direction as the primary coil) may be incorporated into the chamber to longitudinally displace the piston in the opposite direction as the primary coil.

With a similar arrangement, the solenoid may be located more proximally in the catheter shaft and the actuation member would serve as the solenoid core rather than the piston as mentioned above. The coils would be incorporated into or surrounding the shaft and would be operably connected to a driver circuit and power source.

The solenoid may also be incorporated into the proximal assembly to avoid the size restrictions imposed by locating the solenoid into the pressure source or actuation member which are located inside the body during use. The solenoid at the proximal end would function substantially the same as described above, but a relatively large solenoid core connected to the actuation member may be utilized rather than the piston or actuation member as described above. Relatively large solenoid coils may be driven by a similar power source and control system, but a more powerful driver circuit and electrical source may be used since the circuitry is outside the body. It has been shown that solenoid model number 9219 available from Lucas Ledex driven by an Harris 7667 integrated circuit (separated in series by a IRF531 MOSFET) and triggered by a Stanford Research DS335 signal generator provides an oscillatory force to the pressure source when rigidly (or releasably) connected to the actuation member. In particular, with this arrangement, frequencies between 1 Hz (approximate displacement of 0.313 inches at low frequencies) and 60 Hz have been obtained. The corresponding dynamic response is discussed in detail with reference to FIGS. 20 and 21.

It should be noted that the solenoid drive system is not the only means to impart longitudinal oscillation to the actuation member and/or piston. Other oscillation methods such as a cam drive may be employed. Also, it is contemplated that drives capable of generating sonic frequencies may be desirable in order to match the natural resonance of the obstruction being dilated.

Figure 7:
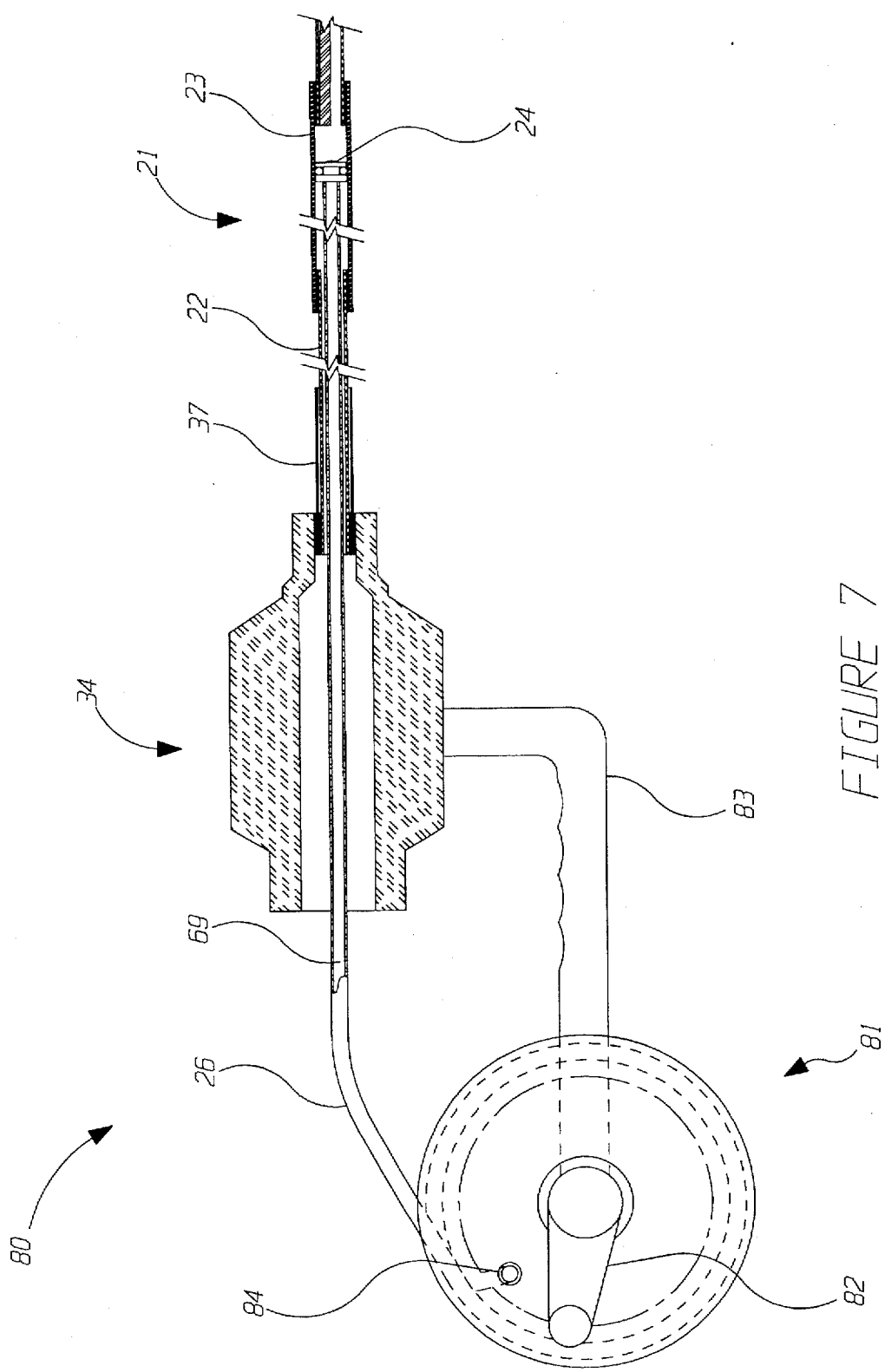
FIGS. 7–13 show sectioned views of various examples of proximal assemblies which may, for example, be incorporated into the catheters described in FIGS. 2a–4.

FIG. 7 shows a first embodiment of a proximal assembly of the present invention. Proximal assembly 80 includes a reel 81 which functions as a receptacle for the actuation member 26. The reel includes a handle 82 which rotates the reel 81 and thus winds or unwinds the actuation member 26 depending on the direction of rotation. The reel 81 is held stationary relative to the catheter shaft 22 and chamber 23 by way of arm 83 which is rigidly connected to the manifold 34. As mentioned previously, the actuation member 26 may be either solid or hollow to accommodate a prep lumen 69 for the introduction of fluid into the pressure source 21 and the inflation lumen. If a hollow actuation member is used, a prep port 84 located on the reel 81 may be utilized for access to the prep lumen 69. The prep port 84 is preferably equipped with a cap to seal off the prep lumen 69 during use.

Figure 8:
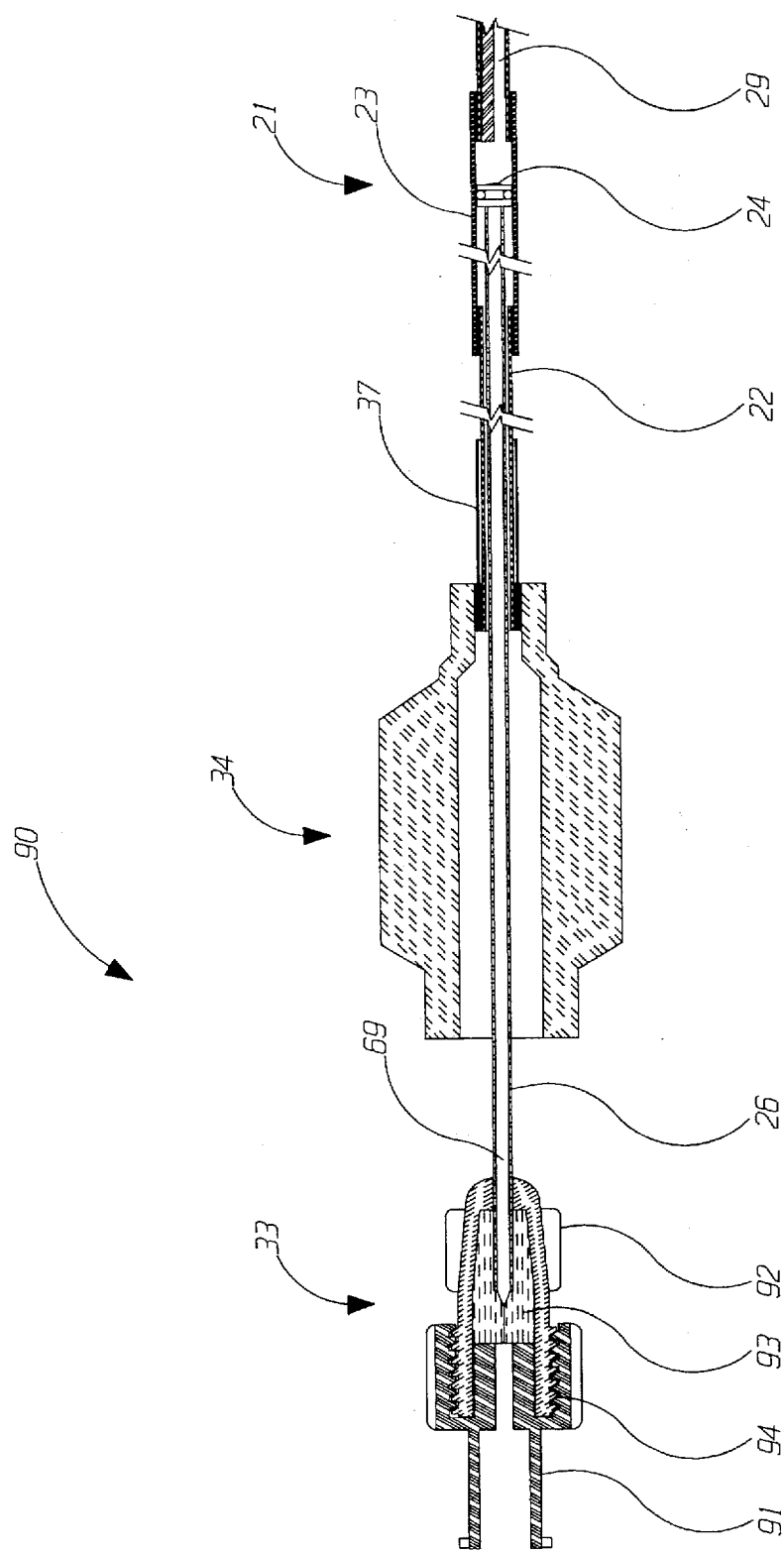

FIG. 8 shows a second embodiment of a proximal assembly of the present invention. Proximal assembly 90 includes a prep manifold 33 connected to the actuation member 26 which allows for fluid to be introduced into the prep lumen 69 prior to in-vivo use and also allows the prep lumen 69 to be closed off prior to in-vivo use. The prep manifold 33 includes a female luer fitting 91 for connection to a conventional prepping syringe. The prep manifold 33 also includes threads 94 so that compression seal 93 closes the prep lumen 69 when the fitting 91 is turned relative to the hub 92.

Figure 9:
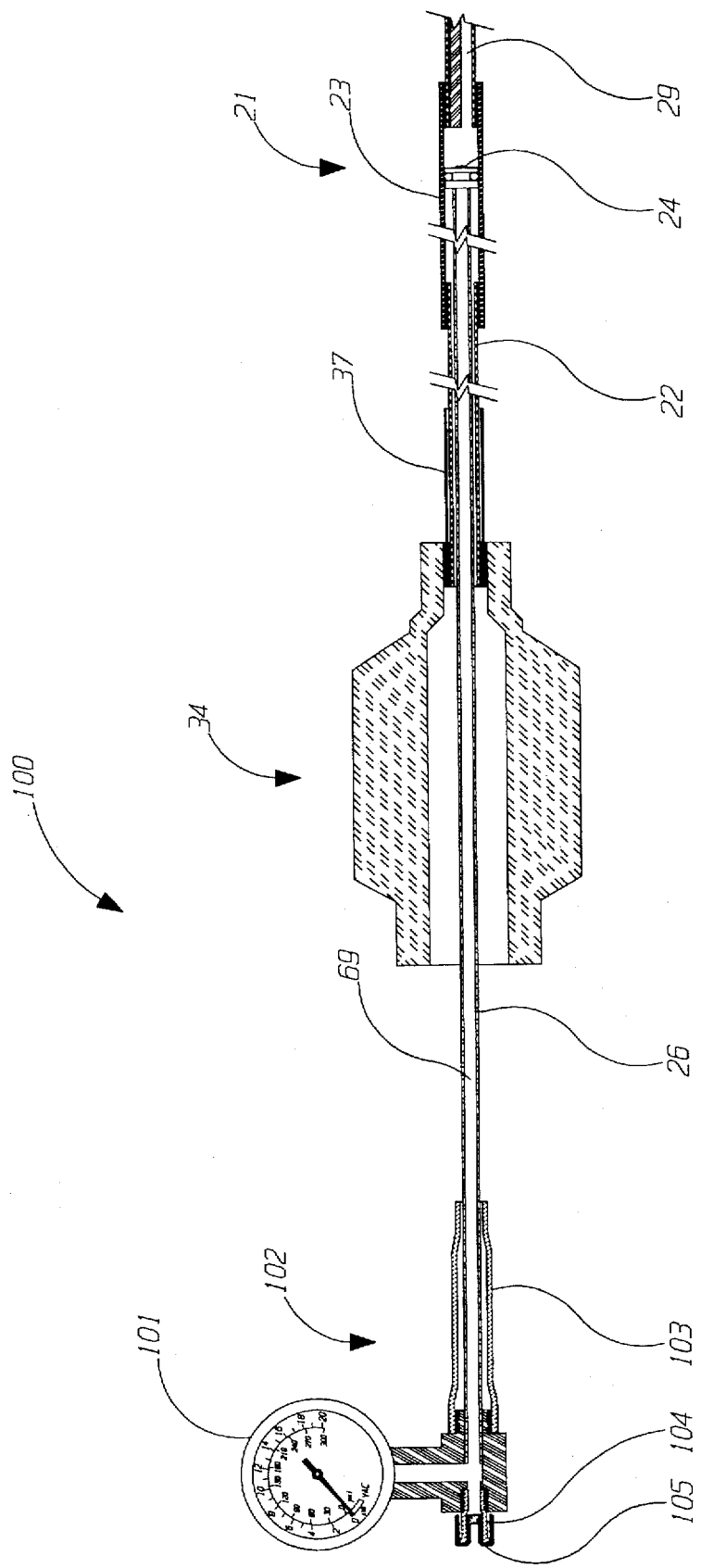

FIG. 9 shows a third embodiment of a proximal assembly of the present invention. Proximal assembly 100 includes a prep manifold 102 connected to the actuation member 26 which includes a fluidic pressure gauge 101 (e.g. Bourdon gauge). The fluidic pressure gauge 101 is in fluid communication with the prep lumen 69 which in turn is in fluid communication with the inflation lumen 29 and the interior of the balloon. With this arrangement, the pressure inside the balloon can be directly monitored by the fluidic pressure gauge 101. Manifold 102 also includes a fitting 105 for connection to a conventional prepping syringe and a cap 105 for closing the prep lumen 69 during use.

The fluidic pressure gauge 101 may be replaced with an electronic pressure transducer and corresponding digital read out. It is also contemplated that the electronic pressure transducer may be mounted inside the chamber 23 and the actuation member could carry electric leads to the proximal end of the catheter for connection to a digital readout.

Figure 10:
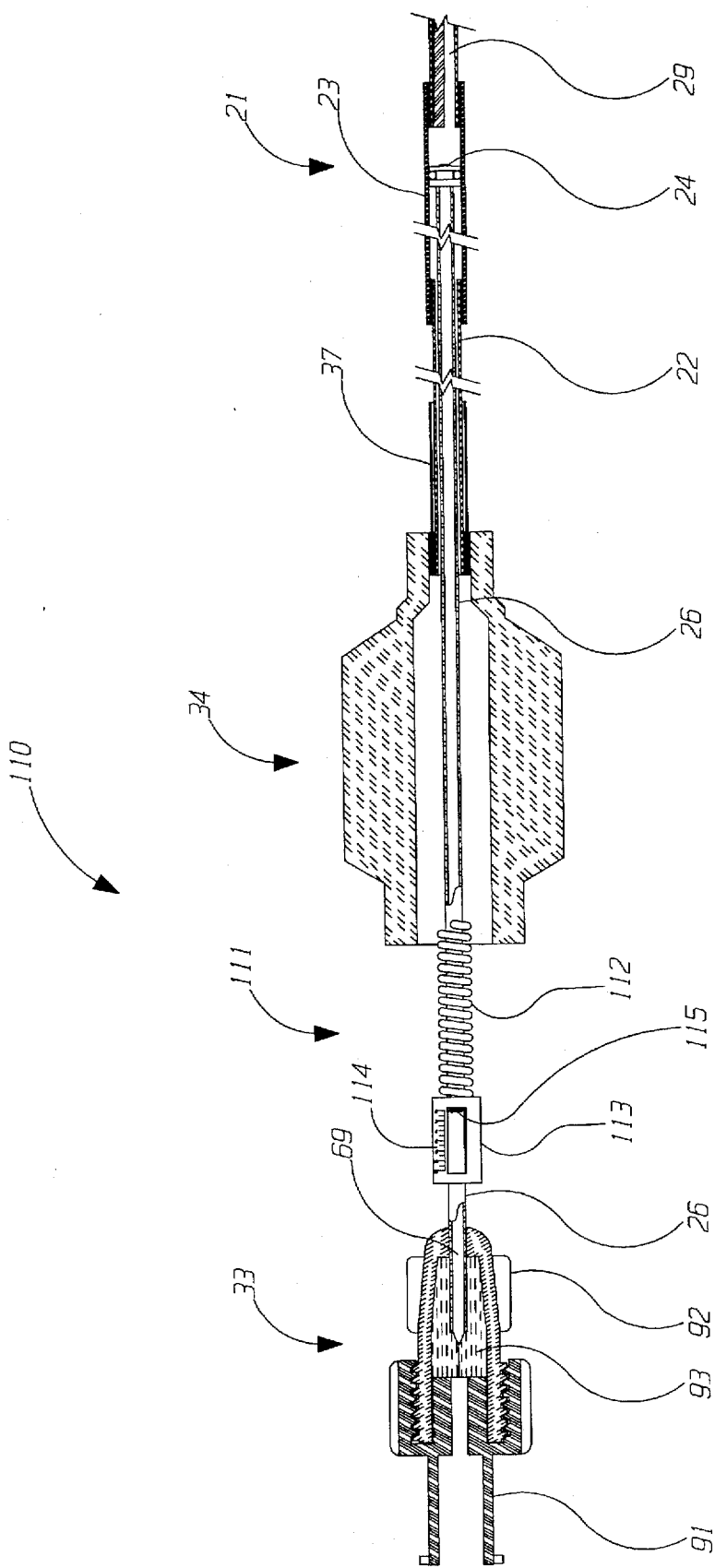

FIG. 10 shows a forth embodiment of a proximal assembly of the present invention. Proximal assembly 110 may include the prep manifold as s discussed with reference to FIG. 8. The proximal assembly 110 also includes a spring pressure gauge 111 which Correlates the compression of the spring 112 to the pressure inside the chamber 23 and thus the pressure inside the balloon. The actuation member 26 is advanced or retracted by gripping the actuator handle 113 rather than the prep manifold 33. The actuator handle 113 is slidably disposed about the actuation member 26 and is rigidly connected to the proximal end of the spring 112. The distal end of the spring 112 is rigidly connected to the actuation member 26. A viewing window is cut into the actuator handle 113 to allow visualization of the indicator arrow 115 disposed on the actuation member 26. As the actuator handle 113 is advanced, the force is transmitted through the spring 112 to the actuation member 26 to the pressure source 21. As pressure builds inside the pressure source 21 and the balloon, the actuation member 26 resists advancement. The resistance to further advancement is felt in the spring 112 which responds by compressing a certain distance. The compression of the spring 112 may be noticed by the change of position of the actuation handle 113 relative to the indicator arrow 115 on the actuation member 26. Knowing the spring constant, the pressure inside the pressure source 21 and inside the balloon may be correlated to the distance the spring 112 is compressed. The correlation may be reflected in the pressure scale 114 disposed on the actuation handle 113, and thus the pressure inside the balloon and pressure source 21 is shown by the position of the indicator arrow 115 relative to the pressure scale 114. The exact same principles may be applied to correlate a vacuum inside the pressure source 21 and balloon to the expansion of the spring 112.

Figure 11:
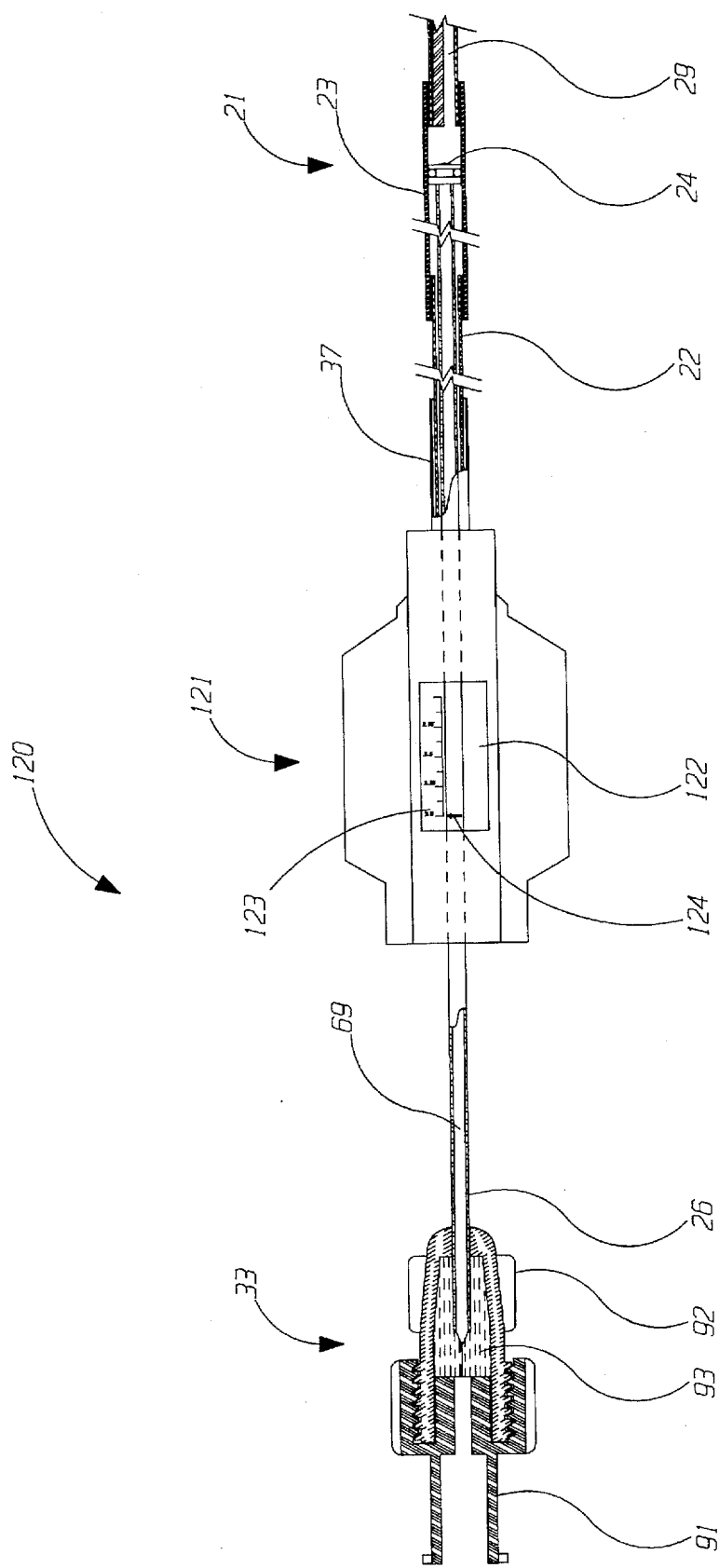

FIG. 11 shows a fifth embodiment of a proximal assembly of the present invention. The proximal assembly 120 may include the prep manifold 33 as discussed with reference to FIG. 8. The proximal assembly 120 includes a shaft manifold 121 similar to the manifold 34 as discussed with reference to FIG. 2a, except that a viewing window 122 is cut into the side to permit viewing of an indicator arrow 124 disposed on the actuation member 26. As the actuation member 26 is displaced either proximally or distally, the piston 24 inside the pressure source 21 displaces a certain volume of fluid which may be correlated to the size increment of the balloon. As such, as the actuation member 26 is displaced, the indicator arrow 124 moves relative to the shaft manifold 121 and the correlated size of the balloon may be shown by balloon sizing scale 123. It should be noted that other similar structures may obtain the basic concept of indicating the size of the balloon by correlating the longitudinal displacement of the actuation member 26 to the size of the balloon. For example, the sizing scale may be located on the actuation member 26 and the indicator may be located on the shaft 22 or the shaft manifold 121.

Figure 12:
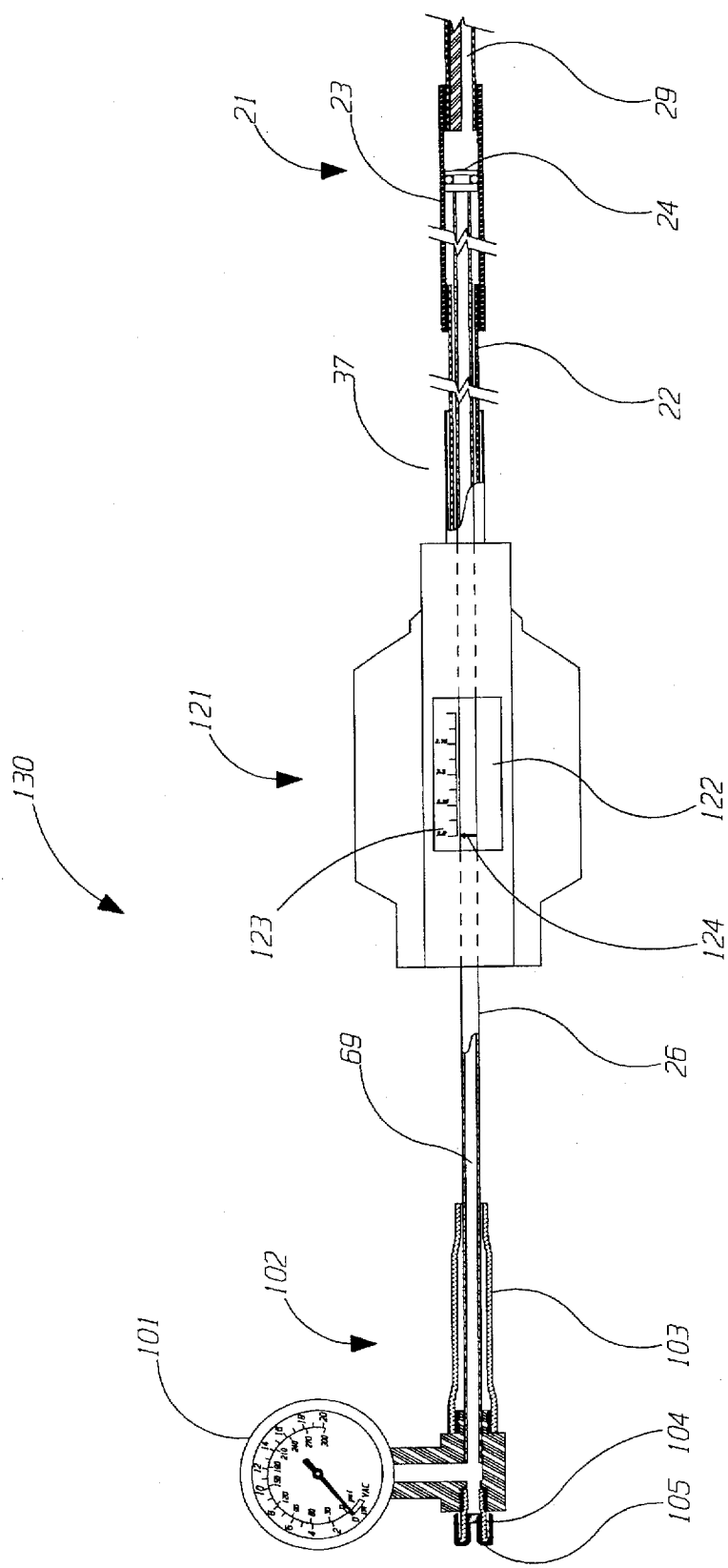

FIG. 12 shows a sixth embodiment of a proximal assembly of the present invention. This embodiment combines some of the features shown in FIGS. 9 and 11. In particular, the proximal assembly 130 includes the pressure gauge manifold 102 as discussed with reference to FIG. 9 and the balloon size manifold 121 as discussed with reference to FIG. 11. The combination allows the treating physician to monitor both the balloon size and the inflation pressure without the need for any ancillary equipment.

Figure 13:
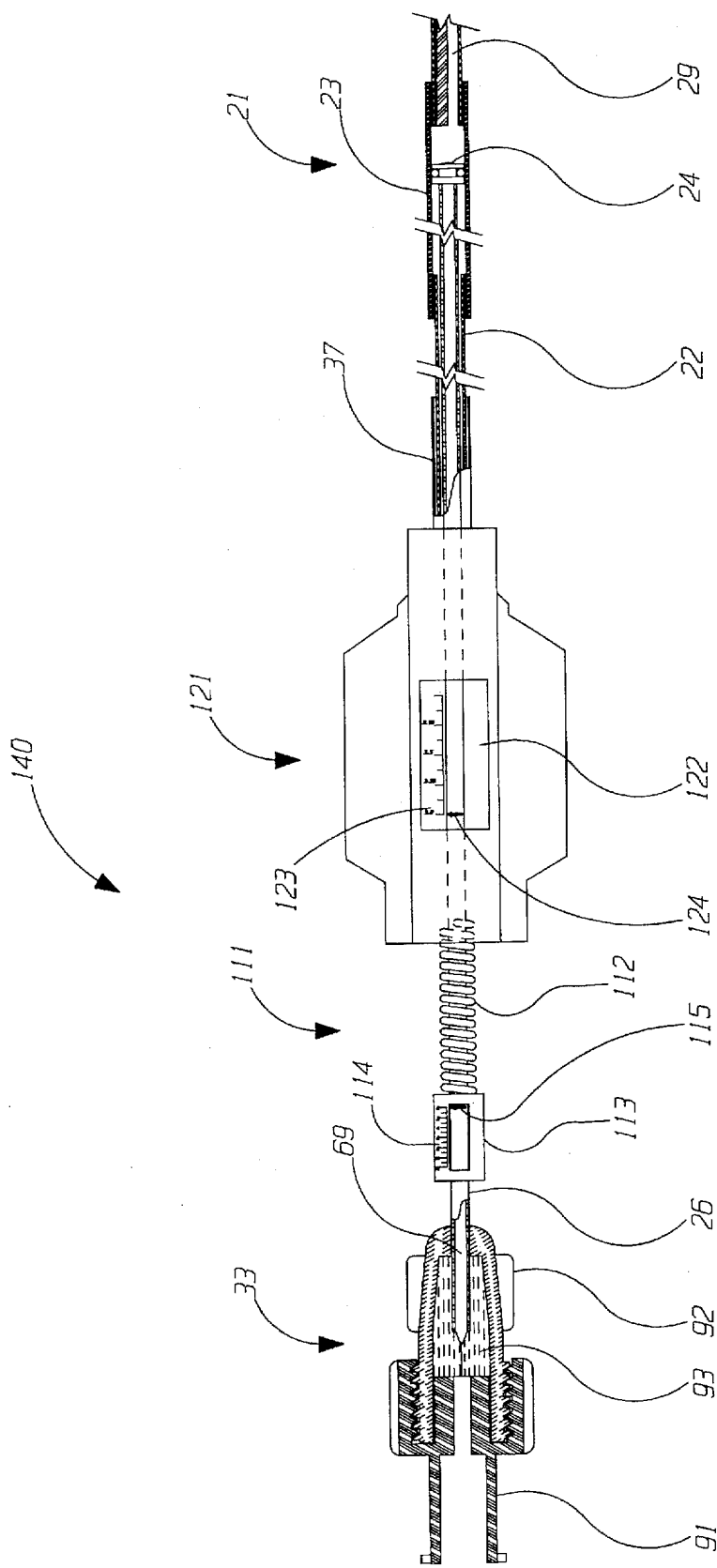

Similarly, FIG. 13 shows a seventh embodiment of a proximal assembly of the present invention. This embodiment combines some of the features shown in FIGS. 8, 10 and 11. In particular, the proximal assembly 140 includes the prep manifold 33 as discussed with reference to FIG. 8, the spring pressure gauge 111 as discussed with reference to FIG. 10, and the balloon size manifold 121 as discussed with reference to FIG. 11. This combination also allows the treating physician to monitor the balloon size and the inflation pressure without the need for any ancillary equipment.

It should be noted that FIGS. 12 and 13 represent mere examples of possible combinations. The individual features of any of the proximal assemblies may be combined to achieve the desired device. In addition, it is contemplated that the pressure gauges and/or the balloon size indicators described above may be either rigidly or releasably attached to the catheter. Furthermore, it is contemplated that the pressure gauge and sizing scale may be at a remote position within view of the treating physician but away from the device.

The various embodiments of the present invention may be used in a variety of ways. The steps associated with inserting the device in-vivo and positioning the balloon across the treatment site are essentially the same as with conventional balloon catheters. However, the steps for prepping the catheter and inflating the catheter are very different. The pressure source, inflation lumen and balloon may be filled with fluid prior to final packaging or may be filled just prior to use by utilizing the prep lumen discussed previously. After the pressure source, inflation lumen and balloon are filled with fluid, the catheter is prepared ("prepped") for use and does not require conventional ancillary devices such as an inflation device.

With the balloon in position invivo, the balloon may be inflated by actuating the actuation member. As discussed previously, this may be done by longitudinal displacement, rotation or magnetic actuation. In the case of longitudinal displacement, the actuation member is pushed distally while holding the shaft and chamber relatively fixed. Similarly, in the case of rotational actuation, the actuation member is rotated while the shaft and chamber are held relatively fixed. Magnetic actuation may be accomplished by activating a solenoid drive which is set to the desired amplitude and frequency. The balloon is inflated to the desired size and/or pressure as indicated by the lo previously described pressure gauges and balloon size indicators. The balloon size may also be monitored by conventional angiography. When desired, the treating physician may deflated the balloon by reversing the actuation steps. In the case of the solenoid drive, the balloon is automatically inflated and deflated in rapid succession. The frequency and or amplitude may be modified during the oscillation or between oscillations. After the treatment is complete, the catheter system is removed substantially the same as conventional balloon catheters.

Figure 14:
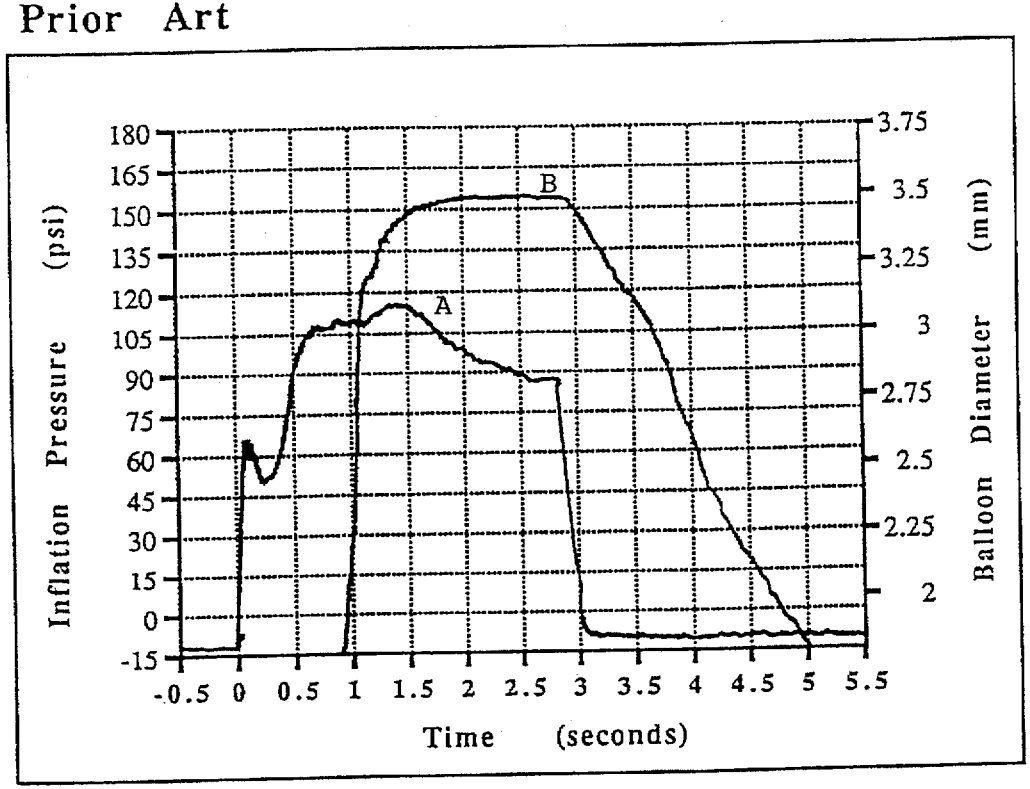
FIGS. 14–21 show the response of the present invention to various conditions versus the response of a prior art catheter system. In particular.
Figure 15:
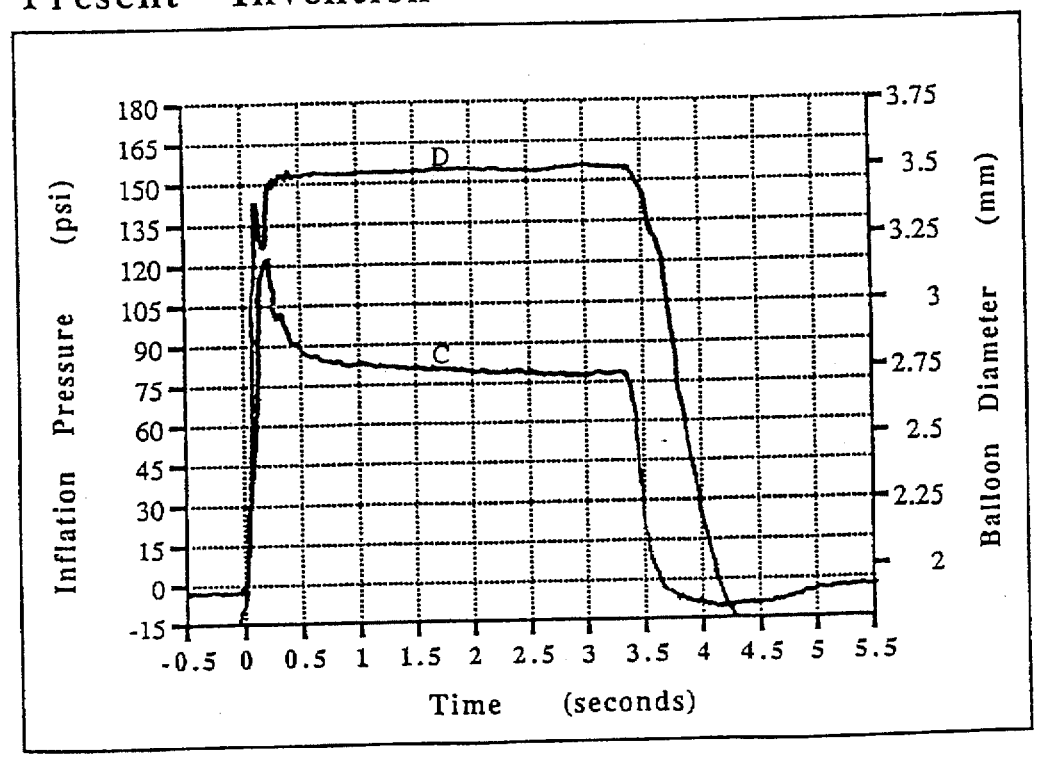

Refer now to FIGS. 14 and 15 which show the balloon response of the present invention versus the a prior art system to a single inflation and deflation. The balloon response Was measured by positioning the balloon in a fixture including a Lucas Schaevitz model 250 DCE linear transducer electrically connected to a TEK 2232 oscilloscope. The linear transducer was positioned to abut one side of the balloon and a stop plate was positioned to abut the other side of the balloon. With this arrangement, changes in balloon diameter caused displacement of the linear transducer as recorded by the oscilloscope. The pressure of both the inflation device (prior art) and the pressure source (present invention) were measured by a Lucas Nova model NPC-102 pressure sensor electrically connected to the TEK 2232 oscilloscope by way of Frequency Devices model 9002 filter instrument.

The prior art device included a SCIMED Cobra 14 3.5 mm×20 mm balloon catheter operably connected to a SCIM ED Encore inflation device. The embodiment of the present invention utilized a 0.054 diameter piston inside a 6.0 inches long chamber which was positioned 30 cm from a 3.5 mm×20 mm balloon. The prior art device was inflated by manually actuating the handle on the inflation device to a specified pressure. The present invention embodiment was inflated by manually pushing the actuation member and holding it at a specified pressure.

FIG. 14 shows the balloon response of the prior art system to a single inflation and deflation. The pressure curve of the inflation device is denoted by the letter A and the balloon-response curve is denoted by the letter B. FIG. 15 shows the balloon response of the present invention to a single inflation and deflation. The pressure curve is denoted by the letter C and the balloon response curve is denoted by the letter D. The balloon response graphs of FIGS. 14 and 15 demonstrate the increased responsiveness of the present invention as compared to the prior art. The prior art device has a inflation time lag of approximately 1.0 seconds from inflation pressure initiation to balloon response and a deflation time lag of approximately 2.0 seconds from deflation pressure initiation to full balloon deflation. By contrast, the present invention has a inflation time lag of approximately 0.1 seconds from inflation pressure initiation to balloon response and a deflation time lag of approximately 0.5 seconds from deflation pressure initiation to full balloon deflation. Thus, in this experiment the inflation response improved 900% and the deflation response improved 300%.

Figure 16:
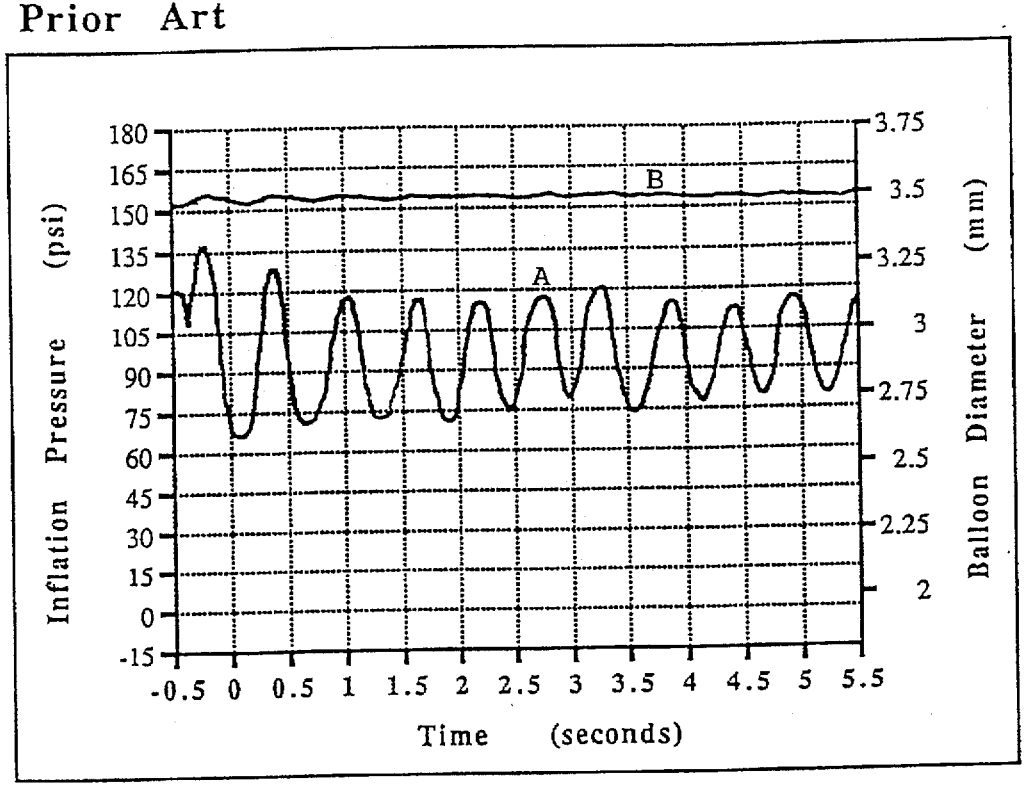
Figure 17:
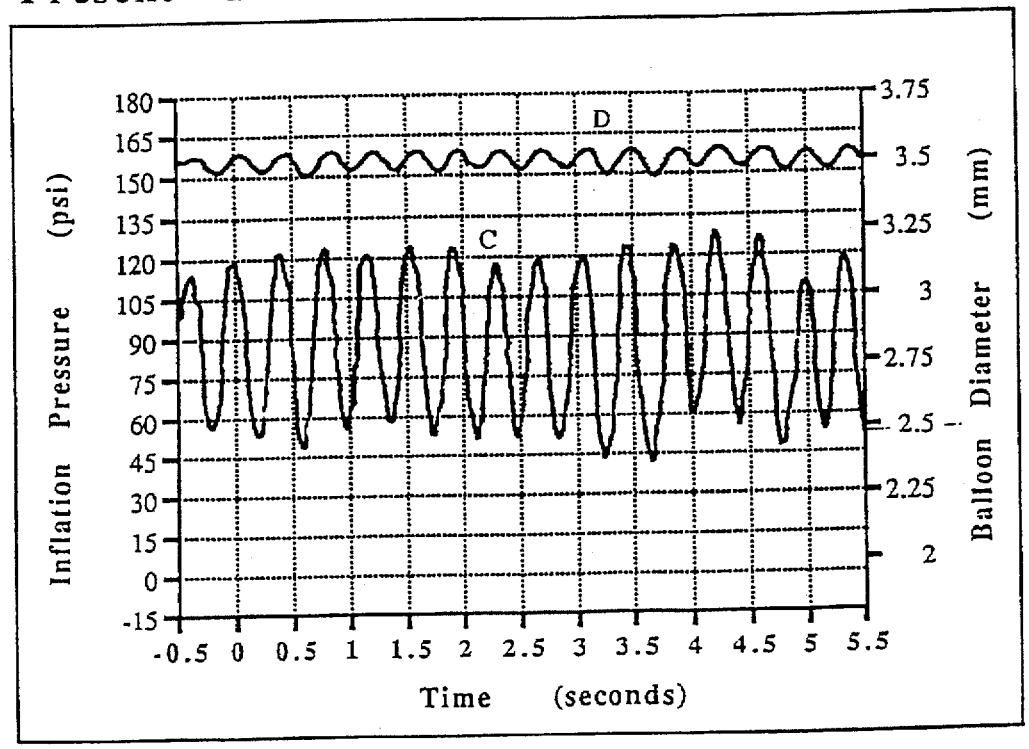

Referring now to FIGS. 16 and 17, the balloon response to cyclic inflation and deflation is shown for a prior art system and an embodiment of the present invention. The same test arrangement and test specimens as discussed with reference to FIGS. 14 and 15 were used for the test corresponding to FIGS. 16 and 17. The inflation device of the prior art system was manually oscillated as was the actuation member on the present invention embodiment. FIG. 16 shows the balloon response of the prior art system to a cyclic inflation and deflation. The pressure curve of the inflation device is denoted by the letter A and the balloon response curve is denoted by the letter B. FIG. 17 shows the balloon response of the present invention to a cyclic inflation and deflation. The pressure curve is denoted by the letter C and the balloon response curve is denoted by the letter D. The balloon response graphs of FIGS. 16 and 17 demonstrate the increased responsiveness of the present invention as compared to the prior art and in particular the benefits of reduced system compliance. The prior art device has an essentially non-responsive balloon to oscillating inflation pressures with an amplitude of approximately 3–4 ATM at a frequency of about 2.2 Hz. By contrast, the present invention embodiment has a noticeably responsive balloon to oscillating inflation pressures with an amplitude of approximately 3–4 ATM at a higher frequency of about 2.75 Hz. Thus, the compliance of the prior art system is sufficiently high to dampen the effect of the inflation pressure, whereas the compliance of the present invention system is sufficiently low to permit effective balloon response to cyclic inflation pressure. This feature may be of particular significance when the pulsating balloon technique is used to atraumatically dilate difficult lesions.

Figure 20:
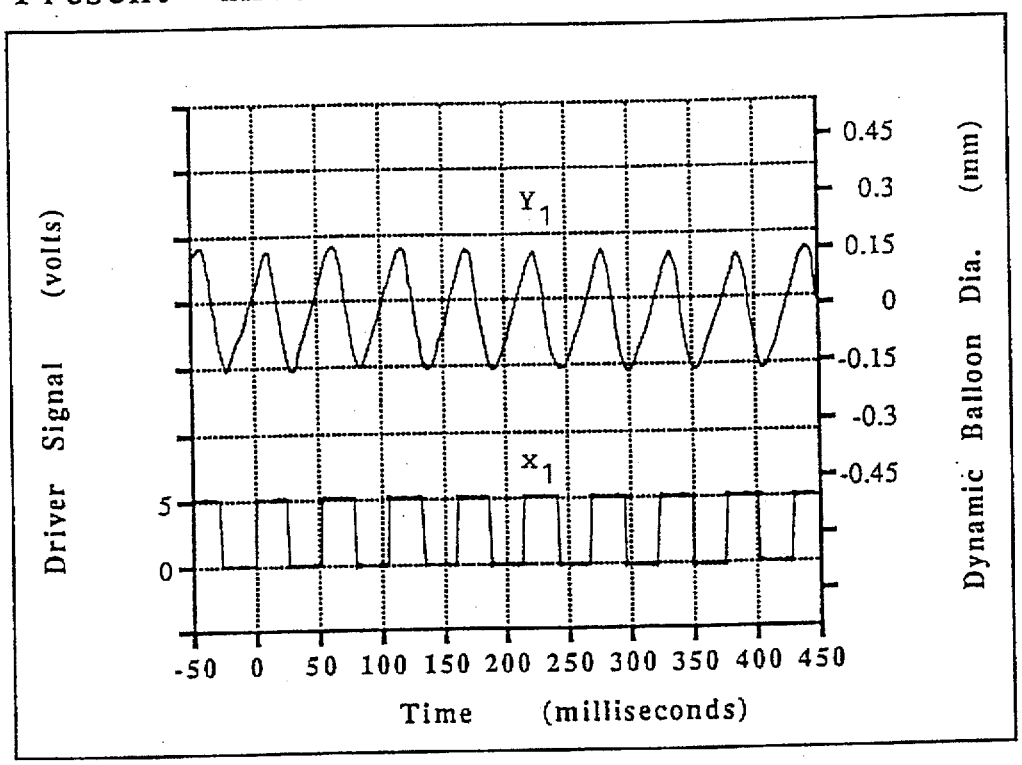
Figure 21:
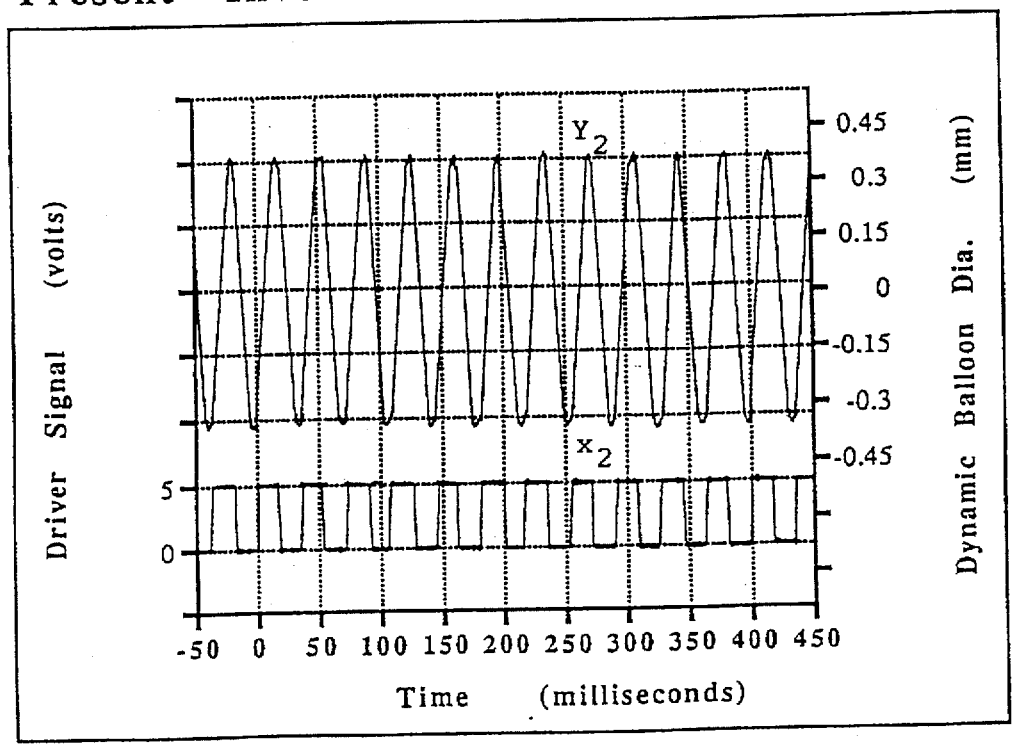

Similar results are demonstrated in FIGS. 20 and 21 which show the dynamic balloon response of the present invention to a solenoid driven pressure source. The solenoid drive system used for this test is described in detail with reference to alternative embodiments of FIGS. 5 and 6. In particular, the test specimen utilized solenoid model number 9219 available from Lucas Ledex driven by an Harris 7667 integrated circuit (separated in series by a IRF531 MOSFET) and triggered by a Stanford Research DS335 signal generator to provide an oscillatory force to the pressure source when rigidly (or releasably) connected to the actuation member. The same balloon response measurement and pressure measurement apparatus as described with reference to FIGS. 14 and 15 was used for the test reflected in FIGS. 20 and 21.

FIG. 20 shows the dynamic balloon response (curve labeled $Y_1$) of an embodiment of the present invention to a solenoid driven at 20 Hz square wave with an amplitude of approximately 5 volts which corresponds to a solenoid displacement of about 0.313 inches (curve labeled $X_1$). The dynamic balloon response has a matched frequency at an amplitude of approximately 0.30 mm. This response results in what essentially feels like a vibrating balloon, which may be used to effectively massage a vascular lesion during dilation and thus perhaps dilate at lower pressures and reduce the potential for abrupt closure or restenosis.

FIG. 21 shows the dynamic balloon response (curve labeled $Y_2$) of an embodiment of the present invention to a solenoid driven at 30 Hz square wave with an amplitude of approximately 5 volts which corresponds to a solenoid displacement of about 0.313 inches (curve labeled $X_2$). The dynamic balloon response has a matched frequency at a relatively large amplitude of approximately 0.65 mm. Thus, without increasing the solenoid amplitude, the balloon response has more than doubled because the input frequency matches the resonance of the catheter system. This can be used to focus significant vibratory energy at the location of the lesion which may improve the ability to dilate difficult lesions such as calcified lesions at relatively low pressures.

It is further contemplated that a drive system operating at higher frequencies (e.g. sonic) may be employed to cause correspondingly higher frequency response of the balloon. With this arrangement, it is believed possible to match the natural resonance of the lesion. Matching the natural resonance of the lesion would allow the treating physician to dramatically affect even the most calcified lesion without disrupting the native vasculature. This allows the physician to effectively treat only the diseased portion of the vessel regardless of the physical integrity of the lesion.

Figure 18:
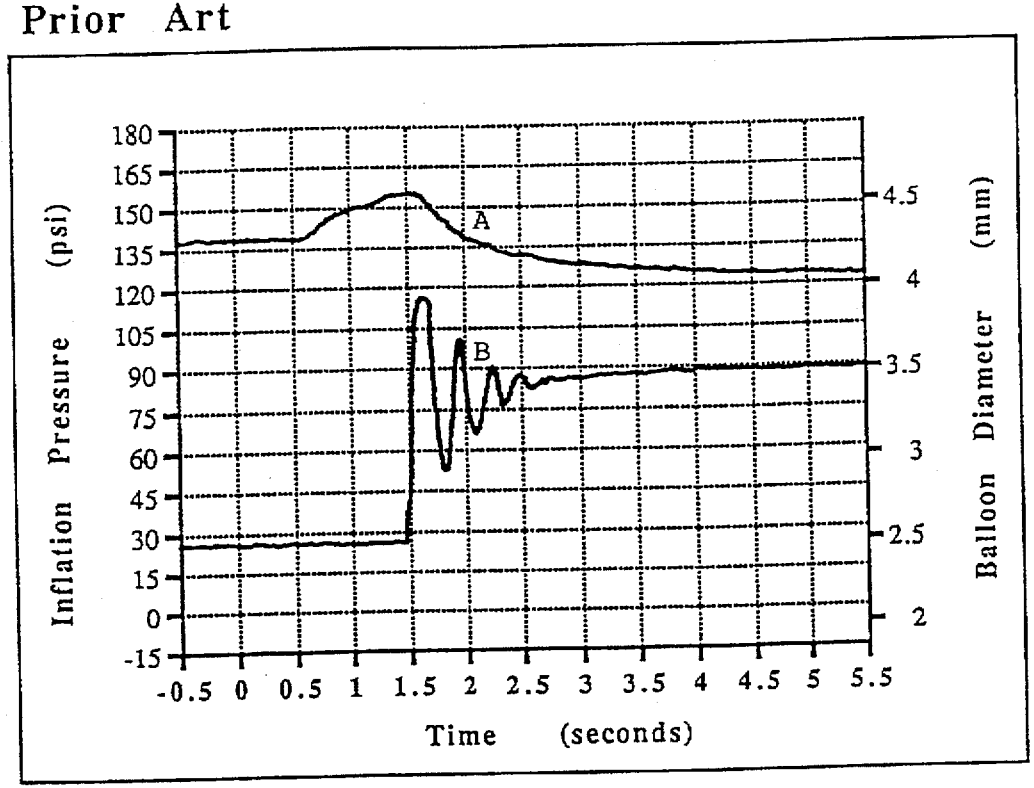
Figure 19:
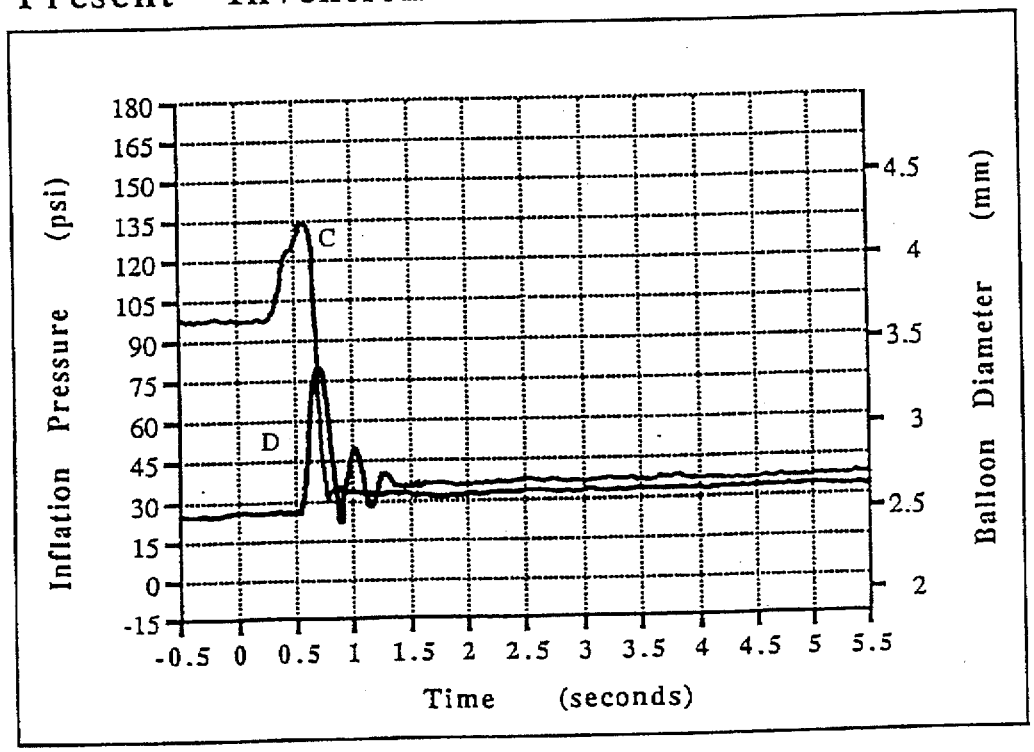

Now refer to FIGS. 18 and 19 which demonstrate the response of a synthetic arterial lesion to balloon dilation. The same test apparatus as described with reference to FIGS. 14 and 15 is used in this experiment except that a synthetic calcium carbonate annular lesion is placed around the balloon. As shown in FIG. 18, the inflation pressure (curve labeled A) of the prior art system is gradually increased by rotating the handle on the inflation device. At approximately 10.4 ATM, the synthetic lesion cracks and the balloon diameter jumps from 2.5 mm to 3.5 mm (curve labeled B). Thus, when the lesion cracks, the balloon continues to grow primarily due to the excessively high stored compliance of the fluid system. By contrast, the balloon diameter (curve labeled B) of the present invention shown in FIG. 19 does not continue to grow more than 0.1 mm. The significantly reduced compliance of the present invention reduces the potential for dissection or crack propagation after the lesion is cracked which in turn increases the potential for favorable clinical results.

Another embodiment of the present invention is contemplated (not shown) which utilizes pressurized gas and a corresponding pressure source in place of the actuation member. A piston and chamber arrangement may be used as described previously but the piston is actuated by the pressurized gas rather than the actuation member. Alternatively, a flexible membrane may be used in place of the piston and chamber. Since the pressurized gas has a relatively low viscosity as compared to conventional inflation liquids, the response of the piston to pressurized gas is almost immediate. By contrast to the actuation means described previously, the overall compliance of this system is higher because gas is relatively compliant. However, the use of gas actuation may in some circumstances increase the responsiveness of the balloon.

While the specification describes the preferred constructions, materials, dimensions, methods of manufacture and methods of practice, those skilled in the art will appreciate the scope and spirit of the invention with reference to the appended claims.

What is claimed is:

1. A balloon catheter insertable into a living body, comprising:
   (a) an elongate shaft having a proximal end and a distal end;
   (b) an inflatable balloon having a proximal end and a distal end, the proximal end of the balloon connected to the distal end of the shaft; and
   (c) a pressure source connected to the shaft, the pressure source including means for limiting balloon overexpansion when the balloon is inflated to dilate a restriction and the restriction yields at a relatively high inflation pressure.

2. A balloon catheter as in claim 1, further comprising:
   (d) a spring tip connected to the distal end of the balloon.

3. A balloon catheter as in claim 1, further comprising:
   (d) a guide wire lumen extending through at least a portion of the elongate shaft.

4. A balloon catheter as in claim 3, further comprising:
   (e) a guide wire lumen access port distal of the proximal end of the elongate shaft.

5. A balloon catheter as in claim 1, further comprising:
   (d) a piston disposed in the pressure source.

6. A balloon catheter as in claim 5, further comprising:
   (e) an actuation member having a proximal end and a distal end, the distal end of the actuation member connected to the piston.

7. A balloon catheter as in claim 6, wherein the actuation member is a solid rod.

8. A balloon catheter as in claim 6, wherein the actuation member is a tube.

9. A balloon catheter as in claim 8, further comprising:
   (f) a valve connected to the proximal end of the actuation member.

10. A balloon catheter as in claim 6, further comprising:
    (f) an actuation member receptacle connected to the proximal end of the actuation member.

11. A balloon catheter as in claim 6, further comprising:
    (f) a balloon size indicator disposed on either the actuation member or the shaft.

12. A balloon catheter as in claim 6, further comprising:
    (f) a pushing member having a proximal end and a distal end, the distal end of the pushing member connected to the pressure source.

13. A balloon catheter as in claim 12, wherein the pushing member is selected from the group consisting of a solid rod, a tube, a braided mesh, and a coil.

14. A balloon catheter as in claim 1, further comprising:
    (d) a pressure gauge operatively connected to the pressure source.

15. A balloon catheter as in claim 14, wherein the pressure gauge is fluidic.

16. A balloon catheter as in claim 14, wherein the pressure gauge is electronic.

17. A balloon catheter as in claim 14, wherein the pressure gauge is a spring gauge.

18. A balloon catheter as in claim 1, further comprising:
   (d) an inflation fluid disposed inside the pressure source, the inflation fluid being disposed inside the pressure source prior to final packaging.

19. A balloon catheter as in claim 1, further comprising:
   (d) an inflation fluid disposed inside the pressure source, the inflation fluid being disposed inside the pressure source just prior to use invivo.

20. A balloon catheter as in claim 5, further comprising:
   (e) an oscillating drive operatively connected to the piston.

21. A balloon catheter as in claim 20, wherein the drive is located near the pressure source.

22. A balloon catheter as in claim 20, wherein the drive is located near the proximal end of the shaft.

23. A balloon catheter as in claim 20, wherein the drive is magnetic.

24. A balloon catheter as in claim 23, wherein the drive is a solenoid.

25. A balloon catheter as in claim 6, further comprising:
   (f) an oscillating drive operatively connected to the actuation member.

26. A balloon catheter as in claim 25, wherein the drive is located near the proximal end of the shaft.

27. A balloon catheter as in claim 26, wherein the drive is magnetic.

28. A balloon catheter as in claim 25, wherein the drive operates at a subsonic frequency.

29. A balloon catheter as in claim 25, wherein the drive operates at a sonic frequency.

30. A method of using a balloon catheter wherein the catheter includes an elongate shaft having a proximal end and a distal end; an inflatable balloon having a proximal end and a distal end, the proximal end of the balloon connected to the distal end of the shaft; and a pressure source connected to the shaft, the method comprising the steps of:
   (i) inserting the balloon catheter into a vascular system of a patient;
   (ii) positioning the balloon adjacent a treatment site inside the vascular system;
   (iii) actuating the pressure source to inflate the balloon to dilate a restriction such that the restriction yields at a relatively high inflation pressure but the balloon does not over-expand thereby reducing the potential for dissection or crack propagation;
   (iv) actuating the pressure source to at least partially deflate the balloon; and
   (v) withdrawing the balloon catheter from the vascular system.

31. A method of using a balloon catheter as in claim 30 wherein the actuation steps are repeated in rapid succession.

32. A method of using a balloon catheter as in claim 31 wherein the actuation steps are repeated at a frequency substantially within the sonic range.

33. A method of using a balloon catheter as in claim 31 wherein the actuation steps are repeated at various frequencies to find and maintain the natural resonance frequency of the treatment site to facilitate atraumatic dilation.

* * * * *

UNITED STATES PATENT AND TRADEMARK OFFICE
CERTIFICATE OF CORRECTION

PATENT NO. : 5,728,064
DATED : March 17, 1998
INVENTOR(S) : BURNS et al.

It is certified that error appears in the above-identified patent and that said Letters Patent is hereby corrected as shown below:

Title page, item [56] References Cited, OTHER PUBLICATIONS, at line 22, "Translumincal" should be --Transluminal--.

On page 1, [57] ABSTRACT, at line 10, "robe" should be --tube--.

At column 1, line 57, ".may" should be --may--.

At column 6, line 63, "transmits" should be --transmit--.

At column 8, line 4, "fie" should be --the--; at line 55, delete "d" after "displacement".

At column 11, line 67, delete "s" after --as--.

At column 12, line 2, "Correlates" should be --correlates--.

At column 13, line 40, delete "lo" after "the"; at line 53, "Was" should be --was--; at line 67 "SCIM" should be --SCIMED--.

At column 14, line 1, delete "ED" before "Encore"; at line 11, "balloon-" should be --balloon--.

Signed and Sealed this

Twenty-fourth Day of November, 1998

Attest:

BRUCE LEHMAN

*Attesting Officer*  *Commissioner of Patents and Trademarks*